United States Patent
Matono et al.

(10) Patent No.: US 11,413,295 B2
(45) Date of Patent: Aug. 16, 2022

(54) ORAL PREPARATION OF OBETICHOLIC ACID

(71) Applicant: Intercept Pharmaceuticals, Inc., New York, NY (US)

(72) Inventors: Mitsuhiro Matono, Osaka (JP); Tetsuya Hayama, Osaka (JP)

(73) Assignee: INTERCEPT PHARMACEUTICALS, INC., Morristown, NJ (US)

( * ) Notice: Subject to any disclaimer, the term of this patent is extended or adjusted under 35 U.S.C. 154(b) by 0 days.

(21) Appl. No.: 16/089,477

(22) PCT Filed: Mar. 30, 2017

(86) PCT No.: PCT/JP2017/013221
§ 371 (c)(1),
(2) Date: Sep. 28, 2018

(87) PCT Pub. No.: WO2017/170858
PCT Pub. Date: Oct. 5, 2017

(65) Prior Publication Data
US 2019/0216826 A1 Jul. 18, 2019

(30) Foreign Application Priority Data
Mar. 31, 2016 (JP) .............................. JP2016-071404

(51) Int. Cl.
*A61K 31/575* (2006.01)
*A61K 47/26* (2006.01)
(Continued)

(52) U.S. Cl.
CPC .............. *A61K 31/575* (2013.01); *A61K 9/14* (2013.01); *A61K 9/1682* (2013.01); *A61K 9/20* (2013.01);
(Continued)

(58) Field of Classification Search
CPC ........ A61K 47/10; A61K 47/26; A61K 47/32; A61K 47/36; A61K 47/38; A61K 9/1682;
(Continued)

(56) References Cited

U.S. PATENT DOCUMENTS 7,910,030 B2   3/2011   Remon et al.
9,375,405 B2   6/2016   Lawrence et al.
(Continued)

FOREIGN PATENT DOCUMENTS

CN   105534932 A   5/2016
CN   105997909 A   10/2016
(Continued)

OTHER PUBLICATIONS

Rojas J, Uribe Y, Zuluaga A.; title: Powder and compaction characteristics of pregelatinized starches; Pharmazie. Jun. 2012; vol. 67(6);pp. 513-517. (Year: 2012).*

(Continued)

*Primary Examiner* — Carlos A Azpuru

(57) ABSTRACT

The present invention pertains to an oral preparation having exceptional elutability, the oral preparation containing obeticholic acid or a pharmacologically acceptable salt thereof, a water-soluble excipient, a disintegrating agent, and a water-soluble polymer binder, wherein the oral preparation is a quick-release tablet.

14 Claims, 5 Drawing Sheets

(51) Int. Cl.

| | |
|---|---|
| *A61K 47/32* | (2006.01) |
| *A61K 47/38* | (2006.01) |
| *A61K 9/20* | (2006.01) |
| *A61K 47/10* | (2017.01) |
| *A61K 47/36* | (2006.01) |
| *A61K 9/28* | (2006.01) |
| *A61K 9/14* | (2006.01) |
| *A61K 9/16* | (2006.01) |

(52) U.S. Cl.
CPC ............... *A61K 9/28* (2013.01); *A61K 47/10* (2013.01); *A61K 47/26* (2013.01); *A61K 47/32* (2013.01); *A61K 47/36* (2013.01); *A61K 47/38* (2013.01)

(58) Field of Classification Search
CPC .............. A61K 9/14; A61K 9/20; A61K 9/28; A61K 31/575; A61K 9/1685; A61K 9/2018; A61K 9/2027; A61K 9/2054; A61K 9/2059; A61K 9/2095; A61K 9/0053; A61P 1/16; A61P 3/06; A61P 29/00; A61P 43/00
See application file for complete search history.

(56) References Cited

U.S. PATENT DOCUMENTS

| | | | |
|---|---|---|---|
| 2004/0028741 A1 | 2/2004 | Fujihara | |
| 2005/0080064 A1 | 4/2005 | Pellicciari | |
| 2010/0130426 A1 | 5/2010 | Young et al. | |
| 2013/0203723 A1* | 8/2013 | Sakuma | A61K 9/1611 514/182 |
| 2013/0345188 A1 | 12/2013 | Steiner et al. | |
| 2014/0148428 A1* | 5/2014 | Pruzanski | A61K 31/575 514/182 |
| 2017/0209377 A1* | 7/2017 | Furo | C08J 3/12 |

FOREIGN PATENT DOCUMENTS

| | | |
|---|---|---|
| JP | H 08291051 A | 11/1996 |
| JP | 2015-071556 A | 4/2015 |
| WO | WO 2004/110431 A1 | 12/2004 |
| WO | WO 2013/192097 A1 | 12/2013 |
| WO | WO 2014/202737 A1 | 12/2014 |
| WO | WO 2015/073231 A1 | 5/2015 |
| WO | WO 2016013675 * | 1/2016 |
| WO | WO 2017/008773 A1 | 1/2017 |

OTHER PUBLICATIONS

Shinichiro Tsue, et al.; title: Evaluation of Direct Compression Tablet prepared by a new Super Fine Powder of Hydroxypropyl Cellulose; Evaluation of HPC-SSL-SFP by Nippon Soda Co., Ltd.; pp. 1-4; Oct. 12, 2011. (Year: 2011).*

Otilia M. Y. Koo etal, title: Investigation into Stability of Poly(Vinyl Alcohol)-Based Opadry® II Films; AAPS PharmSciTech.; vol. 12(2); pp. 746-754, Jun. 2011. (Year: 2011).*

Rojas et al., Title: Powder and compaction characteristics of pregelatinized starches; Pharmazie 67, 2012. (Year: 2012).*

Miyajima, Masaharu et al., "Chapter 1 Jozai Capsule-zai ni Shiyo sareru Tenkazai", Formulation Design and Physicochemical Characterization for Pharmaceutical Excipients, 2016, p. 3-18, (English translation enclosed).

Iyakuhin Tenkabutsu Jiten 2007, Yakuji Nippo Ltd., p. 275, paragraph of Polyvinyl Alcohol (Bubun Kenkabutsu). (English translation enclosed).

Airaksinen Sari, et al. "Excipient selection can significantly affect solid-state phase transformation in formulation during wet granulation." Aaps Pharmscitech, 2005, vol. 6, No. 2, p. E311-E322.

Buhler V. et al. "Polyvinylpyrrolidone Excipients for Pharmaceuticals, Povidone, Crosspovidone and Copovidone", 2005, Springer, ISBN 3-540-23412-8. (Abstract only).

Lyakuhin et al. "Japaneese Pharmaceutical Excipients Dictionary", Edited by International pharmaceutical excipients council Japan, 2007, p. 109113-109114, 120344-120345, (English translation provided).

Kibbe, A.H. "Starch, Pregelatinized", Handbook of Pharmaceutical Excipients, 6th Edition, 2009, p. 691-694.

* cited by examiner

[Figure 1]
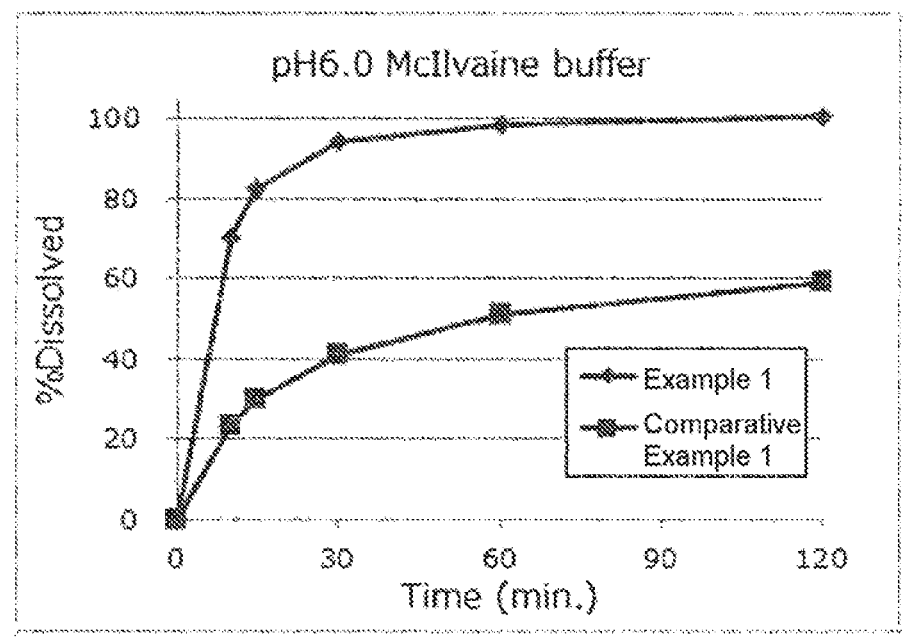
[Figure 2]
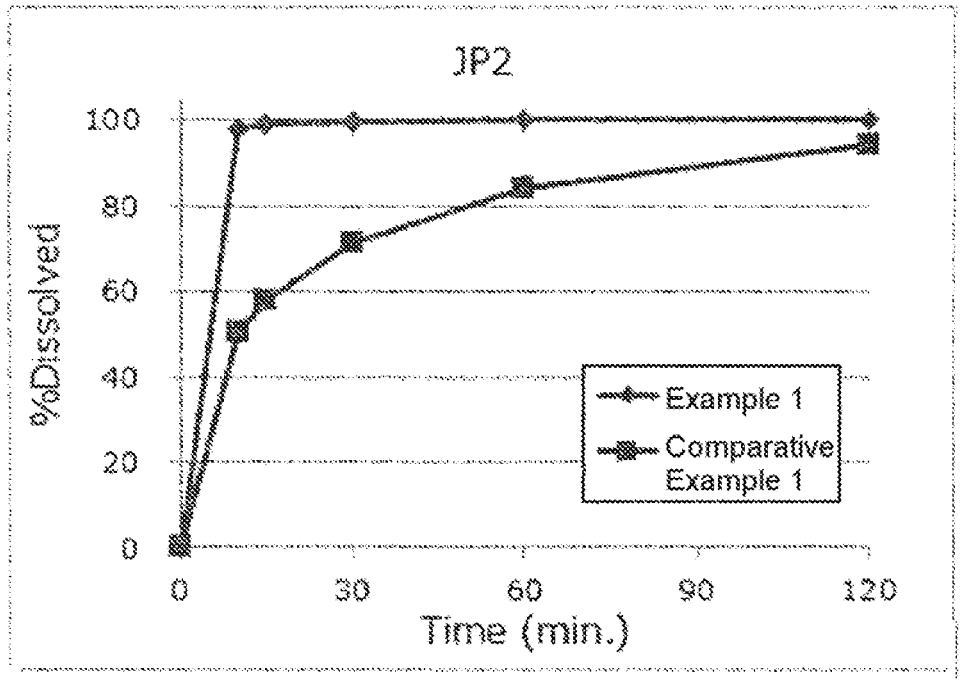

[Figure 3]
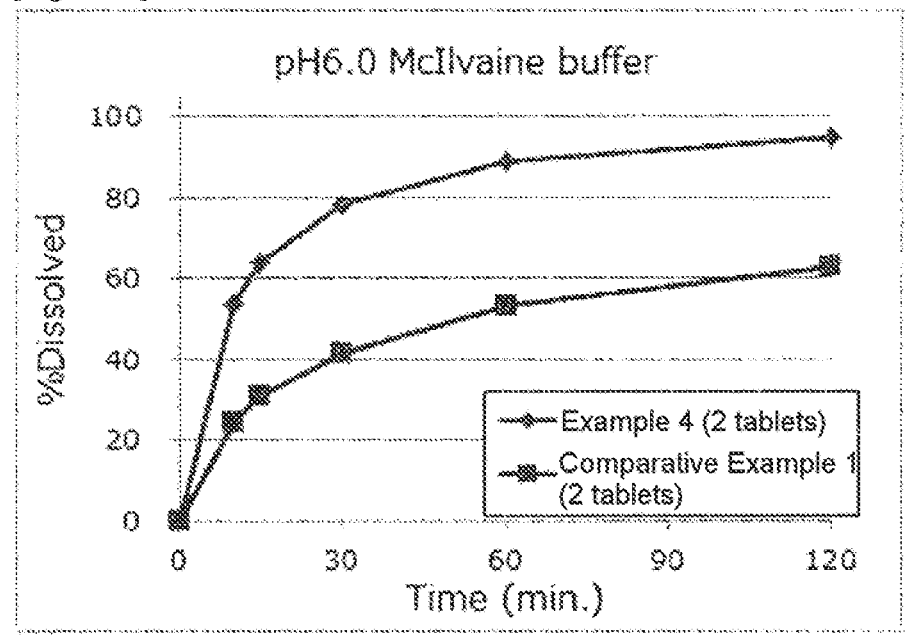
[Figure 4]
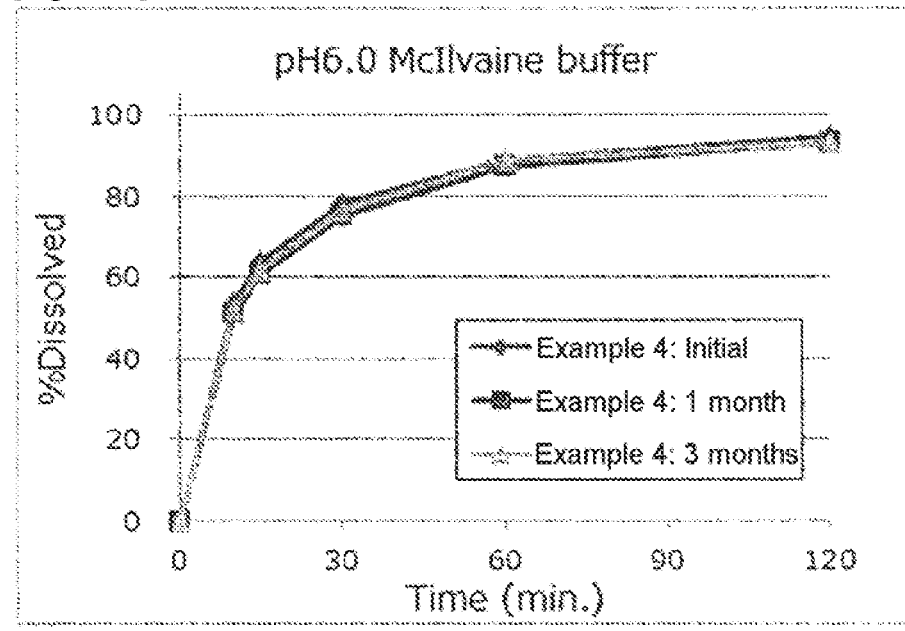

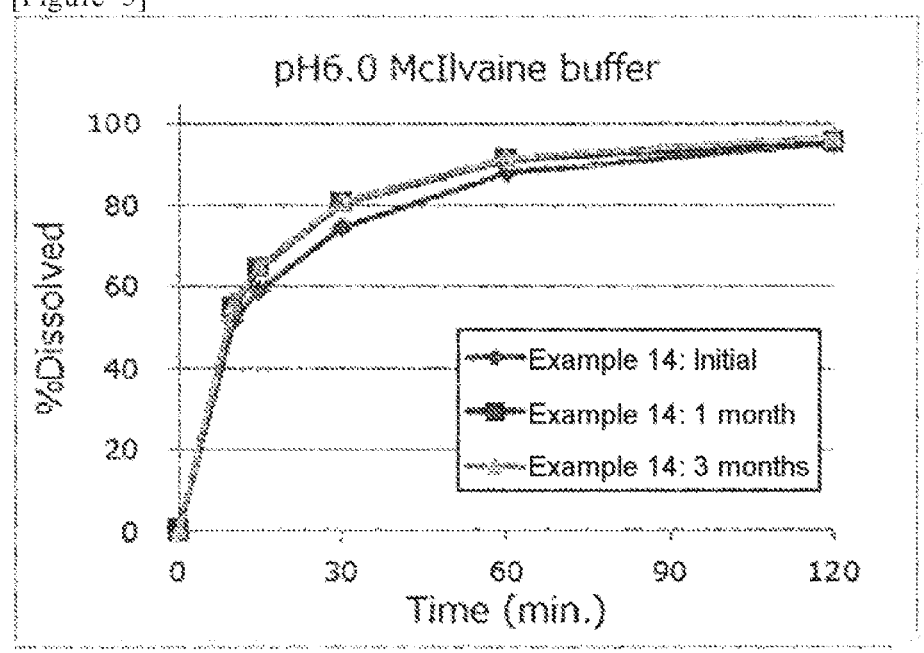
[Figure 5]
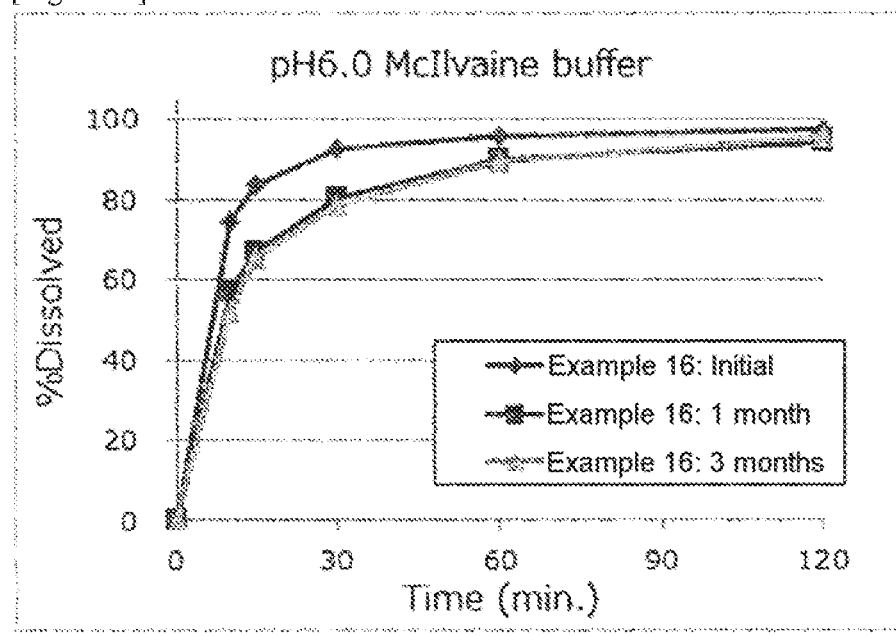
[Figure 6]

[Figure 7]
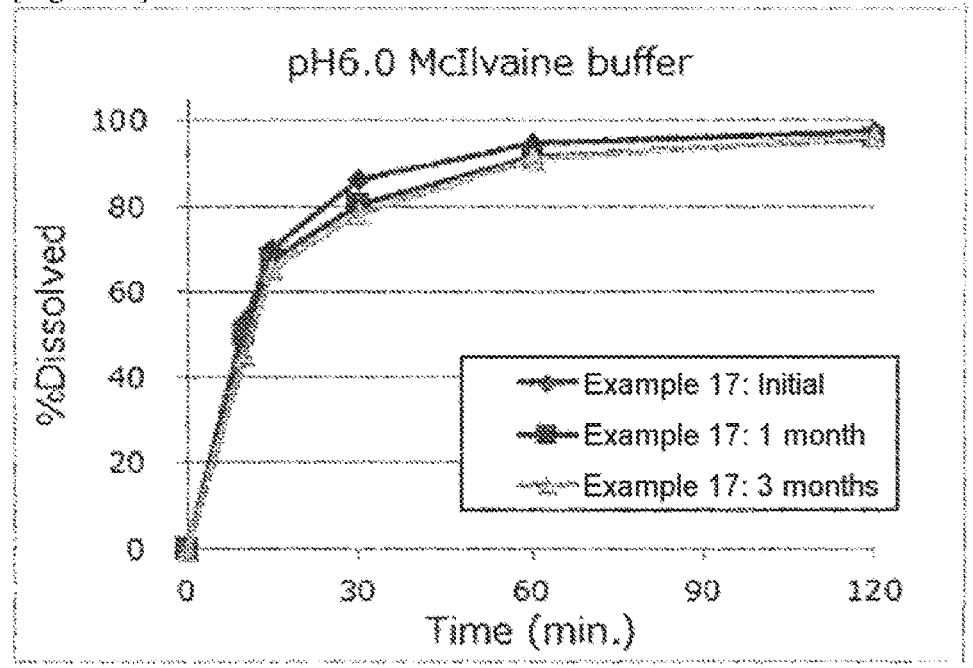
[Figure 8]
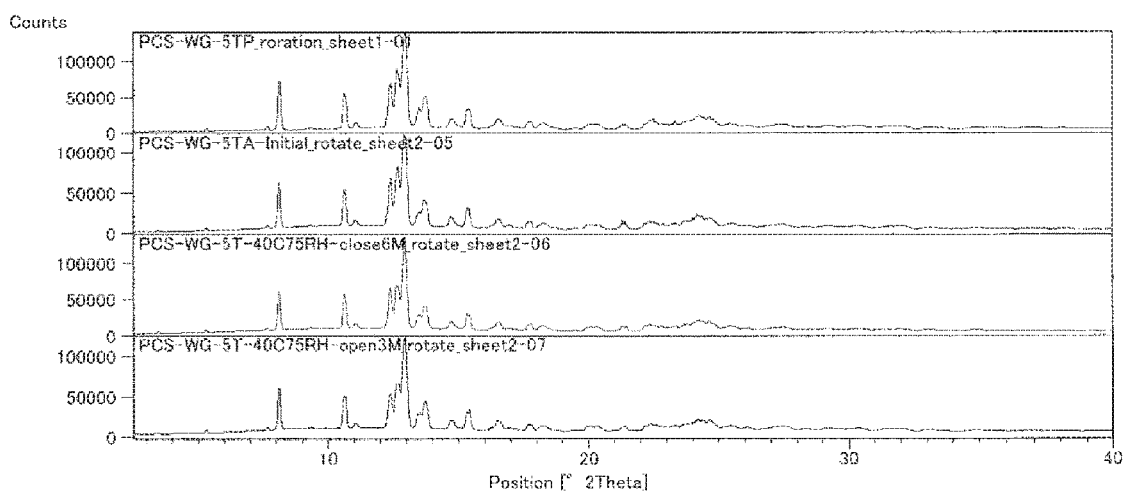

[Figure 9]
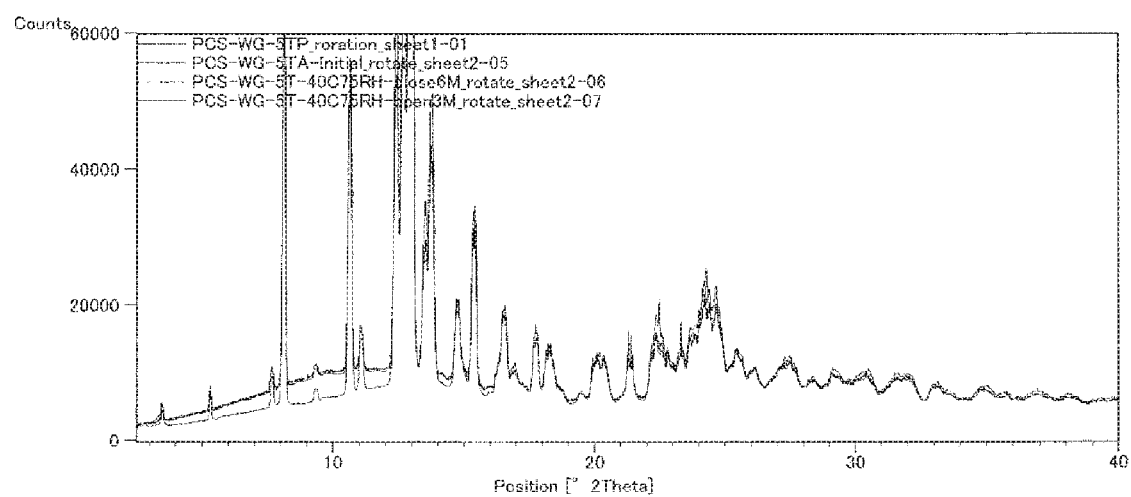

ORAL PREPARATION OF OBETICHOLIC ACID

TECHNICAL FIELD

The present invention pertains to an oral preparation having exceptional elutability, that contains the FXR agonist obeticholic acid, or a pharmacologically acceptable salt thereof, as an active ingredient.

BACKGROUND ART

Obeticholic acid (also known as INT-747 or DSP-1747), which is represented by the following chemical formula, is a compound having pharmacological action as a farnesoid X receptor (FXR)-activating ligand, specifically, an FXR agonist, and shows promise for the treatment of non-alcoholic steatohepatitis (NASH) or primary biliary cirrhosis (PBC), for example.

[Chemical Formula 1]

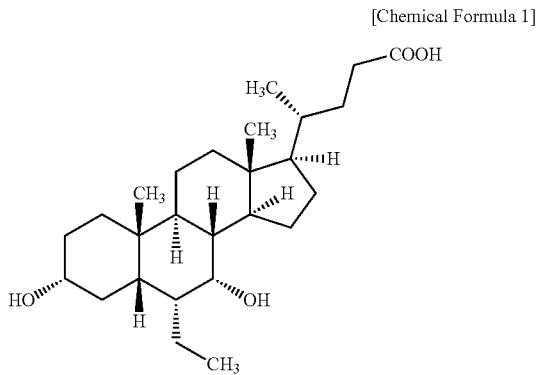

Patent Document 1 indicates that an obeticholic acid compound is preferably administered orally for the prevention and treatment of FXR-mediated diseases or conditions, and describes tablets, capsules, wafer capsules, and lozenges as common examples of preparations suitable for oral administration, but does not specifically describe the formulation components, for example, for an oral preparation containing obeticholic acid.

Patent Document 2 discloses tablets that contain obeticholic acid and certain inactive ingredients in certain blended amounts, and discloses microcrystalline cellulose, sodium starch glycolate, magnesium stearate, colloidal silicon dioxide, and Opadry II (registered trademark) as such inactive ingredients, but does not describe the performance, such as the elutability, of the tablets. In addition, the disclosed components of the tablets do not include any corresponding to a water-soluble polymer binder.

There is a need to develop an oral preparation having better performance, such as elutability, to ensure that obeticholic acid, which promises to be useful for the treatment of NASH or PBC, for example, is more effectively provided in the form of a pharmaceutical.

PRIOR ART DOCUMENTS

Patent Documents

[Patent Document 1] Japanese Patent No. 4,021,327
[Patent Document 2] WO2013/192097 (Japanese Translation of PCT International Application No. 2015-52162)

DISCLOSURE OF INVENTION

Technical Problem

An object of the present invention is to provide an oral preparation having exceptional elutability, that contains obeticholic acid or a pharmacologically acceptable salt as an active ingredient, as well as a method for the manufacture thereof. Another object is to provide an oral preparation having exceptional elution stability. Yet another object is to provide an oral preparation having exceptional bioavailability, and a method for the manufacture thereof.

Solution to Problem

Upon diligent inquiry intended to solve the aforementioned problem, the inventors discovered that the problem could be solved by the following means.

Specifically, the invention is as follows.

[1] An oral preparation, comprising obeticholic acid or a pharmacologically acceptable salt thereof, (i) a water-soluble excipient, (ii) a disintegrating agent, and (iii) a water-soluble polymer binder.

[2] The oral preparation of [1], wherein the (i) water-soluble excipient is a sugar or a sugar alcohol.

[3] The oral preparation of [1] or [2], wherein the sugar or sugar alcohol is mannitol or lactose.

[4] The oral preparation of any of [1] through [3], wherein the sugar or sugar alcohol is lactose.

[5] The oral preparation of any of [1] through [4], wherein the (ii) disintegrating agent is selected from any one or more of starches, sodium croscarmellose, carmellose, low-substituted hydroxypropyl cellulose, and crospovidone.

[6] The oral preparation of any of [1] through [5], wherein the (ii) disintegrating agent is selected from any one or more of starches, low-substituted hydroxypropyl cellulose, and crospovidone.

[7] The oral preparation of [5] or [6], wherein the starch is a pre-gelatinized starch.

[8] The oral preparation of [7,] wherein the starch is partly pre-gelatinized starch.

[9] The oral preparation of any of [1] through [4], wherein the (ii) disintegrating agent comprises two different types, (iia) disintegrating agent A and (iib) disintegrating agent B.

[10] The oral preparation of [9], wherein (iia) disintegrating agent A is any of starches, sodium croscarmellose, carmellose, calcium carmellose, sodium carmellose, crospovidone, low-substituted hydroxypropyl cellulose or sodium carboxymethyl starch, and (iib) disintegrating agent B is any disintegrating agent other than disintegrating agent A from among starches, sodium croscarmellose, carmellose, calcium carmellose, sodium carmellose, crospovidone, low-substituted hydroxypropyl cellulose or sodium carboxymethyl starch.

[11] The oral preparation of [9] or [10], wherein (iia) disintegrating agent A is any of starches, carmellose, or low-substituted hydroxypropyl cellulose.

[12] The oral preparation of any of [9] through [11], wherein (iia) disintegrating agent A is any of starches or low-substituted hydroxypropyl cellulose.

[13] The oral preparation of any of [9] through [12], wherein (iia) disintegrating agent A is a starch.

[14] The oral preparation of any of [10] through [13], wherein the starch is a pre-gelatinized starch.

[15] The oral preparation of any of [10] through [14], wherein the starch is partly pre-gelatinized starch.

[16] The oral preparation of any of [9] through [12], wherein (iia) disintegrating agent A is low-substituted hydroxypropyl cellulose.
[17] The oral preparation of any of [9] through [16], wherein (iib) disintegrating agent B is any of crospovidone, sodium croscarmellose, or sodium carboxymethyl starch.
[18] The oral preparation of any of [9] through [17], wherein (iib) disintegrating agent B is crospovidone or sodium croscarmellose.
[19] The oral preparation of any of [9] through [18], wherein (iib) disintegrating agent B is crospovidone.
[20] The oral preparation of any of [1] through [19], wherein the (iii) water-soluble polymer binder is a polyvinyl alcohol-based resin.
[21] The oral preparation of [20], wherein the polyvinyl alcohol-based resin is a polyvinyl alcohol, polyvinyl alcohol derivative, or polyvinyl alcohol copolymer.
[22] The oral preparation of [20] or [21], wherein the polyvinyl alcohol-based resin is a polyvinyl alcohol.
[23] The oral preparation of [20] or [21], wherein the polyvinyl alcohol-based resin is a polyvinyl alcohol derivative.
[24] The oral preparation of [20] or [21], wherein the polyvinyl alcohol-based resin is a polyvinyl alcohol copolymer.
[25] The oral preparation of any of [1] through [24], wherein the obeticholic acid or pharmacologically acceptable salt thereof is an amorphous form.
[26] The oral preparation of any of [1] through [25], wherein the obeticholic acid or pharmacologically acceptable salt thereof is obeticholic acid.
[27] The oral preparation of any of [1] through [26], wherein the preparation is a tablet.
[28] The oral preparation of [27], wherein the components of the oral preparation of [1] through [26] are contained in an uncoated tablet portion.
[29] The oral preparation of [28], wherein the preparation is a film-coated tablet.
[30] A method for manufacturing an oral preparation, characterized in that obeticholic acid or a pharmacologically acceptable salt thereof is granulated by means of a wet granulation method.
[31] A method for manufacturing the oral preparation of any of [1] through [29], characterized in that obeticholic acid or a pharmacologically acceptable salt thereof is granulated by means of a wet granulation method.
[32] The manufacturing method of [30] or [31], wherein the wet granulation method is a batch-type granulation method.
[33] The manufacturing method of [32], wherein the batch-type granulation method is a fluid bed granulation method or a high-shear granulation method.
[34] The manufacturing method of [30] or [31], wherein the wet granulation method is a continuous granulation method.
[35] The manufacturing method of [34], wherein the continuous granulation method is a double screw wet granulation method.
[36] The manufacturing method of any of [30] through [35], wherein the obeticholic acid or pharmacologically acceptable salt thereof is an amorphous form.
[37] The manufacturing method of any of [30] through [36], wherein the obeticholic acid or pharmacologically acceptable salt thereof is obeticholic acid.

Advantageous Effects of the Invention

The discovery of a preparation having better elutability than preparations that have been prepared on the basis of the disclosures in Patent Document 2 was a problem at the Lime that the invention of the present application was examined. As a result of diligent inquiry, the present inventors discovered that the preparation of the invention of the present application, which is characterized by, for example, the use of a structure that is different from that of preparations disclosed in Patent Document 2, specifically, the use of a water-soluble polymer binder, makes it possible to provide an oral preparation having exceptional elutability, that contains obeticholic acid as an active ingredient. It was furthermore discovered that an oral preparation having exceptional elution stability and bioavailability could be provided. In a specific further preferred embodiment of the present invention, the use of a combination of certain inactive ingredients, for example, makes it possible to provide a preparation having particularly exceptional elutability, elution stability, and bioavailability.

Patent Document 2 also indicates that obeticholic acid is used in a preparation in an amorphous form (also referred to as amorphous or non-crystalline form) in development and in preparations (referred to as "non-crystalline Form 1" in Patent Document 2).

It is generally known that compounds in amorphous form are more advantageous in terms of better solubility compared with compounds in crystal form, but are unstable (or have inferior stability) in two respects: due to energy-instability, the compound per se Lends to decompose and the form Lends to become crystalline. Amorphous compounds also suffer a rapid loss of rigidity and viscosity when heated, and the "glass transition point" (temperature at which the fluidity of a material increases or the temperature at which a material starts to solidify when cooled, similar to the "melting point" of crystals) is therefore an important factor when amorphous compounds are used as the active pharmaceutical ingredient in pharmaceutical preparations. Specifically, it is also known that, from the standpoint of the stability of amorphous compounds, a high glass transition point is important, whereas manufacturing in the presence of water results in a decrease in the glass transition point. The use of water is therefore generally considered to be taboo in processes for producing preparations of amorphous active pharmaceutical ingredients. This has resulted in the use of a dry granulation method, in which no water or water-soluble polymer binders are used, as the method for granulating the preparations containing amorphous obeticholic acid (tablets) disclosed in Patent Document 2.

In a further preferred embodiment of the present invention, a preparation having the structure of the present invention unexpectedly made it possible to provide the exceptional preparation noted above without compromising the stability in terms of the two respects noted above (compound decomposition and change to crystal form), even when amorphous obeticholic acid was produced using a wet granulation method (in which the presence of water is a concern), leading to the discovery of a preferred embodiment of the present invention using a wet granulation method which is more desirable for this preparation.

Furthermore, even though batch-type granulation methods are primarily used as wet granulation methods, the use of a continuous granulation method that would allow the preparation to be more efficiently manufactured was also investigated in the invention of the present application (the invention of the present application is by no means limited to this), and it was discovered that an oral preparation having particularly exceptional elution stability can be provided without compromising the elutability after long-term storage even when a continuous granulation method is used as the wet granulation method.

BRIEF DESCRIPTION OF THE DRAWINGS

FIG. 1 compares the elutability of Example 1 and Comparative Example 1 in McIlvaine buffer (pH 6.0).

FIG. 2 compares the elutability of the preparation in Example 1 and the preparation in Comparative Example 1 in Japanese Pharmacopoeia Disintegration Test Solution 2 (referred to below as JP2).

FIG. 3 compares the elutability of the preparation (1 tablet) in Example 4 and the preparation (2 tablets) in Comparative Example 1 in McIlvaine buffer (pH 6.0).

FIG. 4 shows the elutability of the preparation in Example 4 after being stored under open conditions (referred to below as "open") at 40° C. and 75% RH (relative humidity).

FIG. 5 shows the elutability of the preparation in Example 14 after open storage at 40° C. and 75% RH.

FIG. 6 shows the elutability of the preparation in Example 16 after open storage at 40° C. and 75% RH.

FIG. 7 shows the elutability of the preparation in Example 17 after open storage at 40° C. and 75% RH.

FIG. 8 shows the results of X-ray powder diffraction (XRPD) for the initially prepared (initial) product of the preparation in Example 4, two stored products of the preparation in Example 4 (6 months of closed storage at 40° C. and 75% RH; 3 months of open storage at 40° C. and 75% RH), and placebo film-coated (FC) tablets. Shown in descending order are the results for placebo FC tablets, the initial product of Example 4, the products stored closed for 6 months at 40° C. and 75% RH, and the products stored open for 3 months at 40° C. and 75% RH.

In FIG. 9, the XRPD peak shapes of FIG. 8 are superimposed over each other.

DESCRIPTION OF EMBODIMENTS

The present invention is described in further detail below.
(a) Obeticolic Acid or Pharmacologically Acceptable Salts Thereof As used in the present specification, "obeticholic acid" refers to a compound having the following chemical structure.

[Chemical Formula 2]

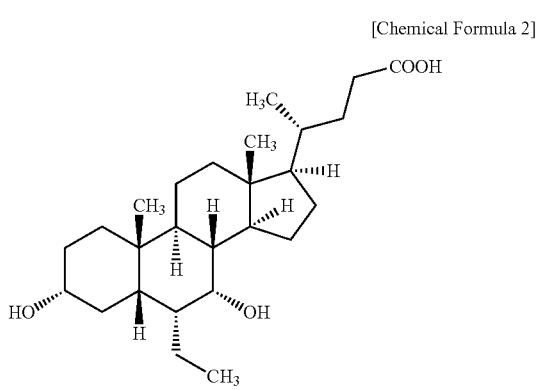

Other chemical names, names, and abbreviations of obeticholic acid include 6α-ethyl-3α, 7 α-dihydroxy-5β-cholan-24-oic acid, 3α,7α-dihydroxy-6α-ethyl-5β-cholan-24-oic acid, 6α-ethylchenodeoxycholic acid, 6-ethyl-CDCA, 6ECDCA, cholan-24-oic acid, 6-ethyl-3, 7-dihydroxy-(3α, 5β,6α, 7α)-, OCA, DSP-1747, and INT-747. The CAS registration number of obeticholic acid is 459789-99-2. This term encompasses all forms of obeticholic acid (e.g., amorphous, crystalline, and various crystal polymorphisms).

In the present invention, obeticholic acid is handled as an acidic compound, and examples of "pharmacologically acceptable salts of obeticholic acid" include inorganic salts (such as sodium, potassium, lithium, barium, calcium, and magnesium salts) and organic salts (such as pyridinium, picolinum, and triethylammonium salts).

In the present invention, obeticholic acid or pharmacologically acceptable salts thereof include solvates thereof. Examples of solvents that can be used to form solvates include, but are not limited to, water as well as physiologically acceptable organic solvents such as ethanol, acetone, ethyl acetate, and hexane.

In the present invention, obeticholic acid (free form) is particularly preferred as the obeticholic acid or pharmacologically acceptable salt thereof. In the present invention, amorphous obeticholic acid (also referred to as amorphous or non-crystalline form) is particularly preferred.

In the present invention, the obeticholic acid or pharmacologically acceptable salt thereof may be milled to the desired particle size before the particles are manufactured, as needed. The material is milled with a common method such as milling using a pulverizing mill, but extremely fine particles may also be used. For example, the diameter of particles representing ≥90% of particles based on volume ratio (D90) may be 100 μm, and the average particle diameter based on volume ratio (50% particle size; D50) may range, for example, from 0.1 to 20 μm, and preferably from 1 to 10 μm. When the preparation is in the form of tablets, for example, the amount in which the obeticholic acid or pharmacologically acceptable salt thereof is blended, based on total tablet weight, may be selected, for example, from 0.1 to 50 wt %, and preferably from 1 to 30 wt %, while 3 to 20 wt % is particularly preferred. When the preparation is in the form of tablets, for example, the content of the obeticholic acid or pharmacologically acceptable salt thereof per tablet may be 0.1 to 160 mg, 1 to 80 mg, preferably 2.5 to 40 mg or 2.5 to 50 mg, and particularly preferably 2.5 to 20 mg, 5 to 20 mg, 2.5 to 25 mg or 5 to 25 mg. Alternatively, tablets may be in the form of, for example, 1 mg tablets, 1.25 mg tablets, 2 mg tablets, 2.5 mg tablets, 5 mg tablets, 10 mg tablets, 12.5 mg tablets, 20 mg tablets, 25 mg tablets, 40 mg tablets, 50 mg tablets, 80 mg tablets, or 100 mg tablets, and preferably 2.5 mg tablets, 5 mg tablets, 10 mg tablets, 20 mg tablets, 25 mg tablets, 40 mg tablets, and 50 mg tablets. In particular, 25 mg tablets are preferred.

(b) Water-Soluble Excipient

Examples of water-soluble excipients that can be used in the present invention include water-soluble excipients commonly used in producing preparations, but sugars or sugar alcohols are preferred. Examples of sugars and sugar alcohols include, but are not limited to, mannitol, erythritol, xylitol, maltitol, sorbitol, lactose, sucrose, and trehalose. Mannitol, erythritol, lactose, and trehalose are preferred, mannitol, erythritol, and lactose are furthermore preferred, mannitol and lactose are still furthermore preferred, and lactose is most preferred. These water-soluble excipients can be used singly or in combinations of two or more.

The amount in which the water-soluble excipient is blended in the present invention, based on total tablet weight, may be, for example, 30 to 90 wt %, preferably 40 to 80 wt %, and more preferably 45 to 75 wt %.

(c) Disintegrating Agent

Examples of disintegrating agents that can be used in the present invention include disintegrating agents commonly used in producing preparations, such as starches, low-substituted hydroxypropyl cellulose, carmellose, calcium carmellose, sodium carmellose, crospovidone, sodium croscarmellose, and sodium carboxymethyl starch (also referred to as sodium starch glycolate). In one embodiment of the present invention, the preparation may be sodium carboxymethyl starch-free. As the disintegrating agent, a starch, low-substituted hydroxypropyl cellulose, carmellose, crospovidone, or sodium croscarmellose is preferred, a starch, low-substituted hydroxypropyl cellulose, or crospovidone is more preferred, and a starch or crospovidone is particularly preferred. Starches are more preferably pre-gelatinized starches, and partly pre-gelatinized starch is particularly preferred. These disintegrating agents can be used singly or in combinations of two or more.

When two or more disintegrating agents are combined, two disintegrating agents may be preferably combined, for example, preferably a combination of a starch and crospovidone or a combination of low-substituted hydroxypropyl cellulose and crospovidone, and more preferably a combination of partly pre-gelatinized starch and crospovidone.

The content of the disintegrating agent used in the present invention, based on total tablet weight, may be, for example, 5 to 50 wt %, preferably 5 to 40 wt %, more preferably 10 to 40 wt %, still more preferably 10 to 30 wt %, and even more preferably 10 to 25 wt %.

In another embodiment of the present invention, when two or more disintegrating agents are combined, and particularly when two disintegrating agents, for example, are combined, the content of one disintegrating agent (such as a starch, low-substituted hydroxypropyl cellulose, or partly pre-gelatinized starch), based on total tablet weight, may be, for example, 5 to 50 wt %, preferably 5 to 40 wt %, more preferably 10 to 40 wt %, still more preferably 10 to 30 wt %, and even more preferably 15 to 25 wt %, and the content of the other disintegrating agent (such as crospovidone), based on total tablet weight, may be, for example, 0.1 to 10 wt %, preferably 0.5 to 8 wt %, and more preferably 1 to 5 wt %.

An example of another preferred embodiment of the invention in the present application is to use a combination of two different kinds of disintegrating agents, disintegrating agent A and disintegrating agent B. Examples of disintegrating agent A include starches, sodium croscarmellose, carmellose, calcium carmellose, sodium carmellose, crospovidone, low-substituted hydroxypropyl cellulose, and sodium carboxymethyl starch (also referred to as sodium starch glycolate), at which time examples of disintegrating agent B may be selected from disintegrating agents other than disintegrating agent A, such as starches, sodium croscarmellose, carmellose, calcium carmellose, sodium carmellose, crospovidone, low-substituted hydroxypropyl cellulose, and sodium carboxymethyl starch.

Disintegrating agent A is preferably a starch, carmellose, or low-substituted hydroxypropyl cellulose, and more preferably a starch or low-substituted hydroxypropyl cellulose, while starches are particularly preferred. Starches are more preferably pre-gelatinized starches, and partly pre-gelatinized starch is particularly preferred.

Disintegrating agent B is preferably crospovidone, sodium croscarmellose, or sodium carboxymethyl starch, and more preferably crospovidone or sodium croscarmellose, while crospovidone is particularly preferred.

The content of disintegrating agent A, based on total tablet weight, may be, for example, 5 to 50 wt %, preferably 5 to 40 wt %, more preferably 10 to 40 wt %, and still more preferably 10 to 30 wt %, while 15 to 25 wt % is particularly preferred; the content of disintegrating agent B, based on total tablet weight, may be, for example, 0.1 to 10 wt %, preferably 0.5 to 8 wt %, and more preferably 1 to 5 wt %.

In the present invention, when two or more disintegrating agents are used, such as when disintegrating agent A and disintegrating agent B are used in combination, the total amount of disintegrating agent based on total tablet weight may be, for example, 5 to 60 wt %, preferably 10 to 50 wt %, more preferably 15 to 45 wt %, and still more preferably 15 to 30 wt %, while 20 to 30 wt % is particularly preferred. The proportion (weight ratio) of the combination of disintegrating agent A and disintegrating agent B is not particularly specified but may be, for example, a ratio ranging from 2:1 to 10:1, preferably from 3:1 to 9:1, and more preferably from 4:1 to 8:1.

"Starches" are generally classified into "natural starches" such as corn starch, potato starch, wheat starch, rice starch, and tapioca starch, and "pre-gelatinized starches" that are obtained by the gelatinization of the above, and any may be used, but "pre-gelatinized starches" are preferred. Examples of "pre-gelatinized starches" include the "pre-gelatinized starch" or "partly pre-gelatinized starch" in the Japan Pharmaceutical Excipient Standards, but "partly pre-gelatinized starch" is more preferable.

The pre-gelatinization rate of "pre-gelatinized starches" is, for example, preferably 50 to 100%, more preferably 50 to 95%, and even more preferably 50 to 90%, while 60 to 90% is particularly preferred. Furthermore, the water-soluble portion of "pre-gelatinized starches" is preferably no more than 40%, and more preferably no more than 30%. A powder that has a mean particle size of usually 1 to 1000 μm, preferably 1 to 500 μm, and more preferably 10 to 100 μm may be used as these "pre-gelatinized starches."

The pre-gelatinization rate of "partly pre-gelatinized starch" is, for example, preferably 50 to 95%, and more preferably 60 to 90%. Furthermore, the water-soluble portion of "partly pre-gelatinized starch" is preferably no more than 40%, more preferably no more than 30%, and even more preferably no more than 20%. A powder that has a mean particle size of usually 1 to 1000 μm, preferably 1 to 500 μm, and more preferably 10 to 100 μm may be used as these "partly pre-gelatinized starches." Examples of commercially available "partly pre-gelatinized starch" suitable for the present invention include PCS (tradename, produced by Asahi-Kasei Chemicals Corporation) and Starch 1500 (tradename, produced by Colorcon), while PCS is more preferred. The content of the "starch" used in the present invention, based on total tablet weight, may be, for example, 5 to 50 wt %, preferably 10 to 40 wt %, more preferably 10 to 30 wt %, and still more preferably 15 to 25 wt %.

"Crospovidone" is a crosslinked 1-vinyl-2-pyrrolidone polymer, examples of which comprise the crospovidone in the Japan Pharmaceutical Excipient Standards. Examples of commercially available crospovidone suitable for the present invention include Kollidon CL (tradename, produced by BASF Corporation), Kollidon CL-F (tradename, produced by BASF Corporation), Kollidon CL-M (tradename, produced by BASF Corporation), Kollidon CL-SF (tradename, produced by BASF Corporation), Polyplasdone XL (tradename, produced by ISP), and Polyplasdone XL-10 (tradename, produced by ISP). The content of "crospovidone" used in the present invention, based on total tablet weight, may be for example 0.1 to 10 wt %, preferably 0.5 to 8 wt %, and more preferably 1 to 5 wt %.

"Low-substituted hydroxypropyl cellulose" is a low-substituted hydroxypropyl ether of cellulose, examples of which comprise the low-substituted hydroxypropyl cellulose in the Japan Pharmaceutical Excipient Standards. Examples of commercially available low-substituted hydroxypropyl cellulose suitable for the present invention include LH-11, LH-21, LH-22, LH-B1, LH-31, LH-32, NBD-20, NBD-21, and NBD-22 (tradenames, produced by Shin-Etsu Chemical Co., Ltd.). The content of "low substituted hydroxypropyl cellulose" used in the present invention, based on total tablet weight, may be, for example, 5 to 40 wt %, preferably 10 to 30 wt %, and more preferably 10 to 20 wt %.

(d) Water-Soluble Polymer Binder

Examples of water-soluble polymer binders that can be used in the present invention include water-soluble polymer binders commonly used in producing preparations. Examples include methyl cellulose, hydroxypropyl cellulose, hydroxypropylmethyl cellulose, polyvinyl pyrrolidone, and polyvinyl alcohol-based resins. Methyl cellulose and polyvinyl alcohol-based resins are more preferable. Polyvinyl alcohol-based resins are even more preferable. Preferred examples of polyvinyl alcohol-based resins include polyvinyl alcohol (PVA), polyvinyl alcohol derivatives, and polyvinyl alcohol copolymers. Polyvinyl alcohol is particularly preferred. Water-soluble polymer binders can be used alone or in combinations of two or more. The amount in which the water-soluble polymer binder is blended, based on total tablet weight, may be selected from the range of 0.1 to 10 wt %, preferably 0.2 to 5 wt %, and more preferably 0.5 to 4 wt %, while the range of 1 to 3 wt % is particularly preferred.

Polyvinyl alcohol-based resins refer to polyvinyl alcohol (PVA), polyvinyl alcohol derivatives, and polyvinyl alcohol copolymers, and commercially available types can generally be used. Examples of specific commercial products of polyvinyl alcohol include Gohsenol EG-03P, EG-05P, EG-18P, EG-22P, EG-30P, EG-40P. EG-05PW, EG-30 PW, and EG-40PW by Nippon Synthetic Chemical Industry Co., Ltd. Examples of specific commercial products of polyvinyl alcohol copolymers include Kollicoat (registered trademark) IR, a polyvinyl alcohol-polyethylene glycol graft copolymer by BASF Corporation. Examples of specific commercial products of polyvinyl alcohol derivatives include the polyvinyl alcohol copolymers POVACOAT (trademark) Type F. Type R. and Type L by Daido Chemical Corporation.

Polyvinyl alcohol is usually produced by polymerizing vinyl acetate, which is then completely or partially saponified. The polyvinyl alcohol in the Japan Pharmaceutical Excipient Standards, for example, can be used in the present invention; fully saponified products are defined as having a degree of polymerization of at least 97 mol %, whereas partially saponified products are defined as having a degree of polymerization of 79 to 96 mol %. The degree of saponification of the polyvinyl alcohol in the present invention is not particularly limited, but the use of partially saponified products is preferred.

The viscosity of the polyvinyl alcohol in the present invention is also not particularly limited, but the viscosity at 20° C. in a 4 wt % aqueous solution is preferably 2 to 40 mPa·s, more preferably 3 to 30 mPa·s, even more preferably 4 to 20 mPa·s, and most preferably 4.5 to 6 mPa·s. The viscosity is the value that is determined by the method described in the Japanese Pharmacopoeia Sixteenth Edition, General Tests. Processes and Apparatus, 2.53 Viscosity Determination. Method 1: Viscosity measurement by capillary tube viscometer.

The content of the "polyvinyl alcohol-based resin" used in the present invention, based on total tablet weight, may be, for example, 0.1 to 10 wt %, preferably 0.2 to 5 wt %, more preferably 0.5 to 4 wt %, and even more preferably 1 to 3 wt %.

(e) Lubricant

When the preparation of the present invention is in the form of a tablet, a lubricant can be added as a component in the formulation of the tablets. Depending on the type of active pharmaceutical ingredient or granules, lubricants can be expected to prevent active pharmaceutical ingredients or granules from adhering to pestler and mortars during tableting, resulting in more efficient production of tablets. The type of lubricant in the present invention includes but is not limited to, for example, stearic acid, magnesium stearate, calcium stearate, sodium stearyl fumarate, talc, carnauba wax, and sucrose fatty acid esters. Stearic acid, magnesium stearate, calcium stearate, sodium stearyl fumarate, and sucrose fatty acid esters are preferred; magnesium stearate, calcium stearate, and sodium stearyl fumarate are more preferred; magnesium stearate and sodium stearyl fumarate are even more preferred; and sodium stearyl fumarate is particularly preferred. These lubricants can be used singly or in combinations of two or more. The lubricant may be mixed with the other ingredients prior to tableting, and may be sprayed onto the mortar and pestle during tableting.

When an internal lubrication method is employed, the amount in which the lubricant is blended in the present invention, based on total tablet weight, should be, for example, 0.2 to 3 wt %, preferably 0.3 to 2 wt %, and more preferably 0.5 to 1.5 wt %. When an external lubrication method is employed, the amount based on total tablet weight should be, for example, 0.01 to 1.0 wt %, and preferably 0.05 to 0.5 wt %.

(f) Film Coating Agent

When the preparation of the present invention is in the form of a tablet, the tablet may be an uncoated tablet that may contain the aforementioned (a) obeticholic acid or pharmacologically acceptable salt thereof, (b) water-soluble excipient, (c) disintegrating agent, and (d) water-soluble polymer binder, and that may optionally contain (e) a lubricant; and may alternatively be a tablet comprising a tablet (uncoated tablet) that may contain (a), (b), (c), and (d), and optionally (e), in the form of an uncoated tablet portion, where the surface of the uncoated tablet is film-coated. Tablets having a film coating are referred to as film coated tablets (also referred to as FC tablets in the specification of the present application). Film coating agents include those combining a base such as hypromellose, hydroxypropyl cellulose, polyvinyl pyrrolidone, polyvinyl alcohol, methacrylic acid copolymer L, methacrylic acid copolymer LD, methacrylic acid copolymer S, aminoalkyl methacrylate copolymer RS, or ethyl acrylate-methyl methacrylate copolymer, and a plasticizer such as polyethylene glycol, propylene glycol, triacetin, triethyl citrate, glycerol, glycerol fatty acid ester, or polyethylene glycol. Additives such as titanium oxide, talc, and colorants can also be added. A brightener such as carnauba wax or talc can also be added after film coating. Examples of equipment include devices classified as coating pans. Preferred examples include devices classified as perforated coating systems.

In addition to the above, the following additives can be added, provided that the function of the present invention is not thereby compromised. Examples include sweeteners, flavoring agents, odor enhancing agents, fragrance, fluidizers (such as Aerosil), antistatic agents, colorants, plasticizers, and antiagglomerants.

Although the formulation of the oral preparation of the present invention will differ depending on the desired dosage form, the desired dosage form can be produced in the usual manner. Methods for producing solid preparations are broadly classified into dry granulation methods (without the use of water) and wet granulation methods (with the use of water). The type of method that is used will ordinarily depend on the properties of the active pharmaceutical ingredient.

In the present invention, as noted above, even when amorphous obeticholic acid is manufactured by a wet granulation method, the stability will not be compromised, and the use of a wet granulation method in the amorphous obeticholic acid granulation process is therefore particularly preferred in one embodiment of the prevent invention.

In this embodiment of the present invention, surprisingly, a preparation having exceptional elutability can be manufactured without compromising the stability in terms of the two respects noted above (compound decomposition and change to crystal form) when using amorphous obeticholic acid.

Examples of wet granulation methods that can be used in the present invention include extrusion granulation, fluid bed granulation, roto-granulation, roto-fluid bed granulation, stirred granulation, high shear granulation, melt granulation, spray granulation, and continuous wet granulation. Of these, extrusion granulation, fluid bed granulation, roto-granulation, roto-fluid bed granulation, stirred granulation, high shear granulation, and melt granulation are classified as batch-type granulation methods, whereas continuous wet granulation methods are classified as continuous granulation methods.

Batch-type granulation methods have primarily been used in the past in pharmaceutical preparation manufacturing processes, specifically, wet granulation methods. However, in the case of batch-type granulation methods, the granulator must be scaled up as pilot manufacturing is increased to manufacturing for clinical study use and furthermore to commercial-scale manufacturing. Continuous granulation methods in which wet granulation is carried out continuously have recently been attracting attention as alternatives to the above methods. In continuous granulation methods, scaling up is unnecessary, making it possible to shorten the preparation development period and to improve productivity. Fluid bed granulation and high shear granulation are preferred batch-type granulation methods. Double screw wet granulation (disclosed in U.S. Pat. No. 7,910,030) is a preferred continuous granulation method. Examples of continuous wet granulators used in continuous granulation methods include continuous stirred mixing granulators (CTS-MiGRA System: by Powrex Corporation), double screw extruders, and double screw wet granulators (JP-A 2015-71556: GEA Pharma System, by GEA Group). Even now, batch-type granulation methods are primarily used as wet granulation methods, but in one embodiment of the present invention (although the present invention is not limited to this), a continuous granulation method allowing a preparation to be manufactured more efficiently can also be used.

In a particularly preferred embodiment of the present invention, an oral preparation having exceptional elution stability can be manufactured without compromising the elutability after long-term storage even when a continuous granulation method is used as such a wet granulation method. In the present invention, "elution stability" means that the elutability is not compromised after the preparation has been stored for a long period of time.

Although the invention of the present application is not necessarily limited to these, examples are shown below, where FC tablets, for example, are prepared using a wet granulation method, for example.

(1) Preparation of Aqueous Solution of Water-Soluble Polymer Binder

A water-soluble polymer binder is dissolved in purified water. The amount of water-soluble polymer binder per amount of purified water may be selected from, for example, 1 to 20 wt %, and preferably 2 to 8 wt %.

(2) Preparation of Granules Containing Obeticholic Acid

Granulation is carried out while the water-soluble polymer binder prepared in step (1) above is dispersed in a fluid bed granulator containing obeticholic acid, a water-soluble excipient, and a disintegrating agent.

Examples of granulators include those classified under methods of, for example, fluid bed granulation, high shear granulation, roto-fluid bed granulation, and double screw wet granulation. However, the invention is not limited to these.

When a double screw wet granulation method is used as the granulation method, the method for adding the water-soluble polymer binder may be to add the binder in the form of a powder, in the form of a solution, or in the form of both a powder and solution.

(3) Drying the Granulated Material

The granulated material is dried at reduced or ordinary pressure. The material is dried so that the level of loss on drying, as determined using an infrared aquameter, is no more than, for example, 3 wt %, and preferably no more than 1 to 2 wt %.

(4) Blending the Lubricant

A lubricant is added to and mixed with the granulated material dried in (3) above. The material is mixed using, for example, a mixer classified as a diffusion mixer (tumbler). Specific examples include tumble blenders, V blenders, double cones, and bin tumblers. However, the invention is not limited to these.

(5) Tableting

The above mixture is tableted to prepare tablets. Examples of tableters include tableters classified as, for example, a tablet press. The degree of tableting hardness may be selected, for example, from the range of 30 to 200 N.

(6) Film Coating is Carried Out, as Desired

The tablets may also be film-coated, as needed. Examples of coating devices include devices classified as coating pans. Devices classified as perforated coating systems are preferred.

(7) Drying

The tablets obtained in the manner described above are dried. Drying is carried out at reduced pressure or ordinary pressure, so that the level of loss on drying, as determined using an infrared aquameter, is no more than, for example, 3 wt %, and preferably no more than 1 to 2 wt %.

The oral preparation of the present invention refers to one that is formulated into tablets, capsules, granules, and fine granules. Tablets, capsules, granules, or fine granules may be formulated in the usual manner using, for example, water-insoluble excipients, binders, disintegrating agents, and lubricants in addition to the water-soluble excipient. Tablets are preferred.

EXAMPLES

Examples, test examples, and comparative examples are shown below to explain the present invention in further detail, but the present invention is not limited to these.

Unless otherwise specified, the following additives were used in the examples, test examples, and comparative examples.

Lactose (Pharmatose 200M): DFE Pharma
Partly pre-gelatinized starch (PCS PC-10): Asahi-Kasei Chemicals Corporation
Low-substituted hydroxypropyl cellulose (LH-12): Shin-Etsu Chemical Co., Ltd.
Crospovidone (Polyplasdone XL-10): ISP
Polyvinyl alcohol (partially saponified product) (Gohsenol EG-05P): Nippon Synthetic Chemical Industry Co., Ltd.
Magnesium stearate (Magnesium Stearate (plant-derived)): Taihei Chemical Industrial Co., Ltd.
Hydroxypropylmethyl cellulose (TC-5R): Shin-Etsu Chemical Co., Ltd.
Triethyl citrate (Citroflex-2): Morimura Bros., Inc.
Talc (Tarkan Hayashi): Hayashi Kasei Co., Ltd.
Titanium oxide (Titanium Oxide NA61): Toho Titanium Co., Ltd.
Carnauba wax (Polishing Wax-105): Freund Corporation
Obeticholic acid (purchased from Intercept Pharmaceuticals Inc.) was used in the free form and the amorphous form.

Example 1: Obeticholic acid 10 mg FC tablets

A. Formulation of Film-Coated (FC) Tablets Containing 10 mg Obeticholic Acid

Granules comprising the following composition, uncoated tablets, and FC tablets were prepared, in that sequence.

(A) Granule Formulation and Charge Amount

| (A) Granule formulation and charge amount | | |
|---|---|---|
| | Example 1 | |
| Component | Amount per tablet (mg) | Charge amount (kg) |
| Obeticholic acid | 10.0 | 2.00 |
| Lactose | 93.6 | 18.72 |
| Partly pre-gelatinized starch | 28.0 | 5.60 |
| Crospovidone | 4.2 | 0.84 |
| Polyvinyl alcohol (partially saponified product) | 2.8 | 0.56 |
| Subtotal | 138.6 | 27.72 |

(b) Uncoated Tablet Formulation and Charge Amount

TABLE 2

| Uncoated tablet formulation and charge amount | | |
|---|---|---|
| | Example 1 | |
| Component | Amount per tablet (mg) | Charge amount (kg) |
| Granules | 138.6 | 25.55 |
| Magnesium stearate (plant-derived) | 1.4 | 0.26 |
| Subtotal | 140.0 | 25.80 |

(c) FC Tablet Formulation

TABLE 3

| FC tablet formulation | |
|---|---|
| | Example 1 |
| Component | Amount per tablet (mg) |
| Uncoated tablet | 140.0 |
| Hydroxypropylmethyl cellulose | 3.00 |
| Titanium oxide | 0.85 |
| Triethyl citrate | 0.15 |
| Carnauba wax | trace amount |
| Total | 144.0 |

B. Manufacturing Method
(1) Granulation and Sizing
<Preparation of Binder Solution>
The polyvinyl alcohol water-soluble polymer binder was added to and dissolved in purified water that had been heated to 80° C. The mixture was allowed to cool to room temperature, and purified water was added to prepare a 4% binder solution.
<Granulation>
Other than the polyvinyl alcohol, the formulation was charged in the charge amounts noted in Table 1 into a fluid bed granulator (flow coater, NFLF-30SJC model, by Freund Corporation), and spray granulation was carried out under the following conditions using the binder solution prepared in (1) above to obtain granules.
<Granulation Conditions>
Charge air temperature: 75° C.
Air flow: 6-8 $m^3$/min
Spray rate: 160 g/min
Spray nozzle diameter: 1.8 mm
Spray air pressure: 0.46 MPa
<Sizing>
The resulting granules were sifted using a sanitary vibrating sieve (502 SB model, by Dalton Corporation). A 710 μm screen size was used.
(2) Mixing the Granules and Lubricant
Magnesium stearate was added to the sized granules prepared in (1) above in the charge amount noted in Table 2, and the material was mixed (20 rpm, 5 min) using a volume mixer (110 L, Yamakin Japan Co., Ltd.) to obtain tableting granules.
(3) Tableting
The tableting granules prepared in (2) above were tableted under the following conditions using a rotary tablet press (AQU 30518SW2AII, by Kikusui Seisakusho Ltd.) to obtain approximately 140 mg uncoated tablets (per tablet).
Punch: Round-faced (R) tablet
Punch size: φ7 mm, 10 R
Disk revolutions: 50 rpm
Tableter compression pressure: Tablets were prepared to a tablet hardness of 40 to 120 N.
(4) Coating
<Preparation of Coating Solution>
A coating solution with a solids concentration of 10% was prepared to allow the coating layer having the composition show in Table 3 to be formed. Hydroxypropylmethyl cellulose and triethyl citrate were added to and dissolved in purified water (solution 1). Separately, titanium oxide was added to and suspended/dispersed in purified water (suspension 1). Solution 1 was added to and dispersed in suspension 1, and the solution was sifted using nylon mesh (150#) to prepare a coating solution.

<Coating>

The uncoated tablets prepared in (3) above were coated under the following conditions to a coating agent film quantity of approximately 4 mg using an Aqua Coater (AQC-48/80 model, by Freund Corporation), giving FC tablets. Carnauba wax was added after the drying step in the film coating process.

<FC Conditions>

Charge air temperature: 80':
Air flow: 8.0 m$^3$/min
Pan revolutions: 10 rpm
Spray air flow rate: 130 NL/min
Pattern air flow rate: 60 NL/min
Solution rate: 80 g/min
Spraying distance: 22 cm Obeticholic Acid Solubility Table 4 shows the solubility of obeticholic acid in various test solutions.

TABLE 4

Obeticholic acid solubility

| | Dissolved concentration (μg/mL) |
|---|---|
| JP1 | 4.07 |
| pH 3.0 McIlvaine buffer | 4.43 |
| pH 4.0 McIlvaine buffer | 4.66 |
| pH 5.0 McIlvaine buffer | 11.40 |
| pH 6.0 McIlvaine buffer | 60.65 |
| Water | 21.45 |
| JP2 | 306.50 |

Test Example 1. Dissolution Test

Dissolution tests of the FC tablets prepared above were performed under the following conditions in accordance with the Japanese Pharmacopoeia, Dissolution Test Methods, Method 2.
Test solution: Diluted McIlvaine buffer (pH 6.0)
Paddle revolutions: 50 rpm
Test solution: 900 mL Test Example 2. Dissolution Test Dissolution tests were performed in the same manner as in Test Example 1, except that the test solution was Solution 2 of the Japanese Pharmacopoeia, Disintegration Test (JP2).
Table 5 shows the results of dissolution tests performed in accordance with Test Example 1 and Test Example 2.

TABLE 5

Dissolution tests of FC tablets (10 mg tablets) (dissolution rate: %)

| | Test solution | 0 | 10 | 15 | 30 | 60 | 120 |
|---|---|---|---|---|---|---|---|
| Example 1 | pH 6.0 McIlvaine buffer | 0.0 | 70.1 | 82.7 | 94.3 | 98.7 | 100.5 |
| Example 1 | JP2 | 0.0 | 97.9 | 99.3 | 99.7 | 99.9 | 100.3 |

Comparative Example 1: Obeticholic Acid 10 mg FC Tablets

Patent Document 2 discloses tablets containing 1 to 25 mg of obeticholic acid. More specifically, the document discloses tablets that contain 1 to 25 mg of obeticholic acid, 157 to 185 mg of microcrystalline cellulose, 12 mg of sodium starch glycolate, 2 mg of magnesium stearate, 4 mg of colloidal silicon dioxide, and 8 mg of a coating material (per tablet). Table 6 shows the formulation of the FC tablets containing 10 mg obeticholic acid that were prepared on the basis of the disclosures in Patent Document 2. The FC tablets containing 10 mg obeticholic acid that were used in Comparative Example 1 were prepared with a dry granulation method.

TABLE 6

Formulation of obeticholic acid FC tablets (Patent Document 2)

| Component | Comparative Example 1 Amount (mg) per tablet |
|---|---|
| Obeticholic acid | 10.0 |
| Microcrystalline cellulose | 176.0 |
| Sodium starch glycolate | 12.0 |
| Magnesium stearate | 2.0 |
| Opadry II (registered trademark) White | 8.0 |
| Total | 208.0 |

Table 7 shows the results of dissolution tests performed in accordance with Test Example 1 and Test Example 2.

TABLE 7

Dissolution tests of FC tablets (10 mg tablets) (dissolution rate: %)

| | | 0 | 10 | 15 | 30 | 60 | 120 |
|---|---|---|---|---|---|---|---|
| Comparative Example 1 | pH 6.0 McIlvaine buffer | 0.0 | 23.4 | 29.5 | 40.6 | 51.1 | 59.0 |
| Comparative Example 1 | JP2 | 0.0 | 50.2 | 58.1 | 71.1 | 84.1 | 94.1 |

Table 7 shows the dissolution rate of the conventional obeticholic acid-containing tablets that are based on the disclosures in Patent Document 2. Compared with these tablets, the dissolution of the obeticholic acid-containing tablets of the present invention was much faster, as shown in Table 5; for example, the tablets that were obtained had very exceptional quick-release properties of at least 85% within 30 minutes in diluted McIlvaine buffer (pH 6.0) and within 15 minutes in JP solution 2 (Tables 5 and 7, and FIGS. 1 and 2).

Example 2: Obeticholic Acid 5 mg FC Tablets

FC tablets were obtained in the same manner as in Example 1, except that the obeticholic acid content per tablet was 5 mg, and lactose was used to adjust for the reduced content (replacement formulation).

Example 3: Obeticholic Acid 2.5 mg FC Tablets

FC tablets were obtained in the same manner as in Example 1, except that the obeticholic acid content per tablet was 2.5 mg, and lactose was used to adjust for the reduced content.

Example 4: Obeticholic Acid 20 mg FC Tablets

A. Formulation of FC Tablets Containing 20 mg Obeticholic Acid

Granules comprising the following composition, uncoated tablets, and FC tablets were prepared, in that sequence.

(A) Granule Formulation and Charge Amount

TABLE 8

Granule formulation and charge amount

| | Example 4 | |
|---|---|---|
| Component | Amount (mg) per tablet | Charge amount (g) |
| Obeticholic acid | 20.0 | 128.57 |
| Lactose | 83.6 | 537.43 |
| Partly pre-gelatinized starch | 28.0 | 180.00 |
| Crospovidone | 4.2 | 27.00 |
| Polyvinyl alcohol (partially saponified product) | 2.8 | 18.00 |
| Subtotal | 138.6 | 891.0 |

(b) Uncoated Tablet Formulation and Charge Amount

TABLE 9

Uncoated tablet formulation and charge amount

| | Example 4 | |
|---|---|---|
| Component | Amount per tablet (mg) | Charge amount (g) |
| Granules | 138.6 | 792.00 |
| Magnesium stearate (plant-derived) | 1.4 | 8.00 |
| Subtotal | 140.0 | 800.0 |

(c) FC Tablet Formulation

TABLE 10

FC tablet formulation

| Component | Example 4 Amount (mg) per tablet |
|---|---|
| Uncoated tablet | 140.0 |
| Hydroxypropylmethyl cellulose | 3.00 |
| Talc | 0.61 |
| Titanium oxide | 0.24 |
| Triethyl citrate | 0.15 |
| Carnauba wax | trace amount |
| Total | 144.0 |

B. Manufacturing Method (1) Granulation and Sizing

<Preparation of Binder Solution>

The polyvinyl alcohol water-soluble polymer binder was added to and dissolved in purified water that had been heated to 80° C. The mixture was allowed to cool to room temperature, and purified water was added to prepare a 4% binder solution.

<Granulation>

Other than the polyvinyl alcohol, the formulation was charged in the charge amounts noted in Table 8 into a fluid bed granulator (Multiplex MP-01, by Powrex Corporation), and spray granulation was carried out under the following conditions using the binder solution prepared in (1) above to obtain granules.

<Granulation Conditions>

Charge air temperature: 75° C.
Air flow: 30-50 m$^3$/hr
Spray rate: 8-12 g/min
Spray nozzle diameter: 1.0 mm
Spray pressure: 0.1 MPa
Spray gun position: Intermediate level <Sizing>

The resulting granules were sifted on a mesh having a screen size of 710 μm to obtain sized granules.

(2) Mixing the Granules and Lubricant

Magnesium stearate was added to the granules prepared in (1) above in the charge amount noted in Table 9, and the material was mixed (40 rpm, 5 min) using a small V mixer (Tsutsui Scientific Instruments Co., Ltd.) to obtain tableting granules.

(3) Tableting

The tableting granules prepared in (2) above were tableted under the following conditions using a rotary tablet press (VEL2, by Kikusui Seisakusho Ltd.) to obtain approximately 140 mg uncoated tablets (per tablet).

Punch: Round-faced (R) tablet
Punch size: φ7 mm, 10 R
Disk revolutions: 20 rpm
Tableter compression pressure: Tablets were prepared to a tablet hardness of 60 to 140 N.

(4) Coating

<Preparation of Coating Solution>

A coating solution with a solids concentration of 10% was prepared to allow the coating layer having the composition shown in Table 10 to be formed. Hydroxypropylmethyl cellulose and triethyl citrate were added to and dissolved in purified water (solution 1). Separately, talc and titanium oxide were added to and suspended/dispersed in purified water (suspension 1). Solution 1 was added to and dispersed in suspension 1, and the solution was sifted using nylon mesh (150#) to prepare a coating solution.

<Coating>

The uncoated tablets prepared in (3) above were coated under the following conditions to a coating agent film quantity of approximately 4 mg using a Hi-Coater HCT-30N (by Freund Corporation), giving FC tablets. Carnauba wax was added after the drying step in the film coating process.

<FC Conditions>

Charge air temperature: 85° C.
Air flow: 0.6 m$^3$/min
Pan revolutions: 24 rpm
Spray pressure: 0.15 MPa
Solution rate: 3-5 g/min
Spraying distance: 11 cm

Example 5: Obeticholic Acid 20 mg FC Tablets

FC tablets were obtained in the same manner as in Example 4, except that the partly pre-gelatinized starch content per tablet was 21 mg, and lactose was used to adjust for the difference in the content.

Example 6: Obeticholic Acid 20 mg FC Tablets

FC tablets were obtained in the same manner as in Example 6, except for the change in the FC component.

<Preparation of Coating Solution>

A coating solution with a solids concentration of 15% was prepared to allow the coating layer having the composition show in Table 11 to be formed. Polyvinyl alcohol and triethyl acetate were added to and dissolved in purified water (solution 1). Separately, talc and titanium oxide were added to and suspended/dispersed in purified water (suspension 1). Solution 1 was added to and dispersed in suspension 1, and the solution was sifted using nylon mesh (150#) to prepare a coating solution.

Example 7: Obeticholic Acid 20 mg FC Tablets

FC tablets were obtained in the same manner as in Example 4, except that the partly pre-gelatinized starch content per tablet was 35 mg, and the amount of lactose was reduced to adjust for the increased content.

Example 8: Obeticholic Acid 20 mg FC Tablets

FC tablets were obtained in the same manner as in Example 4, except that the formulation did not contain crospovidone, and the amount of lactose was increased to adjust for the reduced content.

Example 9: Obeticholic Acid 20 mg FC Tablets

FC tablets were obtained in the same manner as in Example 4, except that the content of polyvinyl alcohol per tablet was 1.4 mg, and the amount of lactose was increased to adjust for the reduced content.

Example 10: Obeticholic Acid 20 mg FC Tablets

FC tablets were obtained in the same manner as in Example 4, except that the content of polyvinyl alcohol per tablet was 4.2 mg, and the amount of lactose was reduced to adjust for the increased content.

Example 11: Obeticholic Acid 20 mg FC Tablets

FC tablets were obtained in the same manner as in Example 4, except that the content of magnesium stearate per table was 0.7 mg, and the amount of lactose was increased to adjust for the reduced content.

Example 12: Obeticholic Acid 20 mg FC Tablets

Magnesium stearate 2.1 mg was mixed with the granulated granules prepared in Example 11 to prepare approximately 141.4 mg uncoated tablets. FC tablets were then obtained in the same manner as in Example 11.

Example 13: Obeticholic Acid 2.5 mg FC Tablets

FC tablets were obtained in the same manner as in Example 1, except that the obeticholic acid content per tablet was 2.5 mg, and lactose was used to adjust for the reduced content.

Example 14: Obeticholic Acid 20 mg FC Tablets

FC tablets were obtained in the same manner as in Example 4, except that low-substituted hydroxypropyl cellulose was used instead of partly pre-gelatinized starch, the content of which per tablet was 16.8 mg, and the amount of lactose was increased to adjust for the reduced content.

Table 11 shows the formulations of the obeticholic acid FC tablets obtained in Examples 4-14.

TABLE 11(1)

| | Formulation of obeticholic acid FC tablets (mg) | | | | |
|---|---|---|---|---|---|
| | Component | Example 4 | Example 5 | Example 6 | Example 7 |
| Uncoated tablet portion | Obeticholic acid | 20.0 | 20.0 | 20.0 | 20.0 |
| | Lactose | 83.6 | 90.6 | 90.6 | 76.6 |
| | Partly pre-gelatinized starch | 28.0 | 21.0 | 21.0 | 35.0 |
| | Low-substituted hydroxypropyl cellulose | — | — | — | — |
| | Crospovidone | 4.2 | 4.2 | 4.2 | 4.2 |
| | Polyvinyl alcohol (partially saponified product) | 2.8 | 2.8 | 2.8 | 2.8 |
| | Magnesium stearate (plant-derived) | 1.4 | 1.4 | 1.4 | 1.4 |
| | Hydroxypropylmethyl cellulose | 3.00 | 3.00 | — | 3.00 |
| FC portion | Polyvinyl alcohol (partially saponified product) | — | — | 1.60 | — |
| | Talc | 0.61 | 0.61 | 1.93 | 0.61 |
| | Titanium oxide | 0.24 | 0.24 | 0.32 | 0.24 |
| | Triethyl citrate | 0.15 | 0.15 | 0.15 | 0.15 |
| | Carnauba wax | trace amount | trace amount | trace amount | trace amount |
| | Total | 144.0 | 144.0 | 144.0 | 144.0 |

TABLE 11(2)

Formulation of obeticholic acid FC tablets (mg)

|  | Component | Example 8 | Example 9 | Example 10 | Example 11 |
|---|---|---|---|---|---|
| Uncoated tablet portion | Obeticholic acid | 20.0 | 20.0 | 20.0 | 20.0 |
|  | Lactose | 87.8 | 85.0 | 82.2 | 84.3 |
|  | Partly pre-gelatinized starch | 28.0 | 28.0 | 28.0 | 28.0 |
|  | Low-substituted hydroxypropyl cellulose | — | — | — | — |
|  | Crospovidone | — | 4.2 | 4.2 | 4.2 |
|  | Polyvinyl alcohol (partially saponified product) | 2.8 | 1.4 | 4.2 | 2.8 |
|  | Magnesium stearate (plant-derived) | 1.4 | 1.4 | 1.4 | 0.7 |
|  | Hydroxypropylmethyl cellulose | 3.00 | 3.00 | 3.00 | 3.00 |
| FC portion | Polyvinyl alcohol (partially saponified product) | — | — | — | — |
|  | Talc | 0.61 | 0.61 | 0.61 | 0.61 |
|  | Titanium oxide | 0.24 | 0.24 | 0.24 | 0.24 |
|  | Triethyl citrate | 0.15 | 0.15 | 0.15 | 0.15 |
|  | Carnauba wax | trace amount | trace amount | trace amount | trace amount |
|  | Total | 144.0 | 144.0 | 144.0 | 144.0 |

TABLE 11(3)

Formulation of obeticholic acid FC tablets (mg)

|  | Component | Example 12 | Example 13 | Example 14 |
|---|---|---|---|---|
| Uncoated tablet portion | Obeticholic acid | 20.0 | 2.5 | 20.0 |
|  | Lactose | 84.3 | 101.1 | 94.3 |
|  | Partly pre-gelatinized starch | 28.0 | 28.0 | — |
|  | Low-substituted hydroxypropyl cellulose | — | — | 16.8 |
|  | Crospovidone | 4.2 | 4.2 | 4.2 |
|  | Polyvinyl alcohol (partially saponified product) | 2.8 | 2.8 | 2.8 |
|  | Magnesium stearate (plant-derived) | 2.1 | 1.4 | 1.4 |
|  | Hydroxypropylmethyl cellulose | 3.00 | 3.00 | 3.00 |
| FC portion | Polyvinyl alcohol (partially saponified product) | — | — | — |
|  | Talc | 0.61 | 0.61 | 0.61 |
|  | Titanium oxide | 0.24 | 0.24 | 0.24 |
|  | Triethyl citrate | 0.15 | 0.15 | 0.15 |
|  | Carnauba wax | trace amount | trace amount | trace amount |
|  | Total | 145.4 | 144.0 | 144.0 |

Dissolution tests were performed on the 20 mg obeticholic acid FC tablets obtained in Examples 4-12 and 14 (1 tablet each) and the 10 mg obeticholic acid FC tablets obtained in comparative example 1 (2 tablets). Table 12 shows the results of dissolution tests performed in accordance with Test Example 1. FIG. 3 shows the results of the dissolution tests on Example 4 (1 tablet) and Comparative Example 1 (2 tablets). Table 12 and FIG. 3 show that the dissolution of the obeticholic acid-containing tablets of the present invention was much faster compared with the dissolution rate of the obeticholic acid-containing tablets of Comparative Example 1 (Table 7 and FIG. 2), and that better quick-release tablets were obtained. Even better quick-release tablets were obtained in the examples in which crospovidone was used (examples other than Example 8).

TABLE 12

Dissolution tests of FC tablets (20 mg tablets) (dissolution rate: %)

|  | 0 | 10 | 15 | 30 | 60 | 120 |
|---|---|---|---|---|---|---|
| Example 4 | 0.0 | 53.7 | 63.6 | 78.4 | 89.2 | 94.9 |
| Example 5 | 0.0 | 52.5 | 61.1 | 74.5 | 88.2 | 95.3 |
| Example 6 | 0.0 | 50.5 | 60.1 | 74.4 | 86.9 | 93.9 |
| Example 7 | 0.0 | 50.5 | 60.1 | 74.4 | 86.9 | 93.9 |
| Example 8 | 0.0 | 36.2 | 46.8 | 65.2 | 81.7 | 92.6 |
| Example 9 | 0.0 | 57.8 | 66.4 | 78.9 | 88.0 | 93.9 |
| Example 10 | 0.0 | 39.1 | 52.9 | 72.1 | 87.2 | 95.1 |
| Example 11 | 0.0 | 57.3 | 64.9 | 80.2 | 90.4 | 95.2 |
| Example 12 | 0.0 | 49.8 | 59.0 | 74.6 | 87.7 | 95.2 |
| Example 14 | 0.0 | 51.5 | 59.1 | 74.7 | 87.8 | 95.3 |
| Comparative Example 1 | 0.0 | 24.5 | 30.7 | 41.6 | 53.2 | 62.8 |

In Examples 15-17 below, obeticholic acid-containing tablets were prepared using a double screw wet granulation method. The double screw wet granulator, fluid bed dryer (brand name: ConsiGma-1, GEA Pharma Systems), and peristaltic pump (brand name: Roller Pump RP-1000, by Eyela) disclosed in JP-A 2015-71556 were used in the double screw wet granulation method.

Example 15: Obeticholic Acid 20 mg FC Tablets (Double Screw Wet Granulation Method)

Obeticholic acid 285.7 g, lactose hydrate 1354.29 g. low-substituted hydroxypropyl cellulose 240.0 g, and crospovidone 60.0 g were weighed out and mixed in a plastic bag. The powder mixture was introduced into the powder supply feeder of a double screw wet granulator. The powder mixture was fed at a rate of 20 kg/hour from the powder supply feeder into the chamber, and as 8.5 wt % polyvinyl alcohol aqueous solution was fed therein at a rate of 80 g/min by a peristaltic pump, granulation was continuously carried out for 4 minutes at a screw speed of 700 rpm using the screw structure shown in Table 13. The granulated powder was dried in a fluid bed dryer. 450 g of the dried powder was sized at 1200 rpm using a sizer (brand name: Quadro Comil 197S, by Powrex Corporation), with a grater-type screen (mesh size 1.06 mm) and a compression-type blade. To 396 g of the resulting sized powder, magnesium stearate 4.0 g was added and mixed. In the post-tableting process, FC tablets were obtained in the same manner as in Example 4.

TABLE 13

| Screw structure | XT/6 · N/4 · 60°/1.5T/6 · N/4 · 60°/1.5T/2 · N/6 · 60° |
|---|---|

Example 16: Obeticholic Acid 10 mg FC Tablets (Double Screw Wet Granulation Method)

Obeticholic acid 50.0 g, lactose hydrate 524.0 g, low-substituted hydroxypropyl cellulose 84.0 g, and crospovidone 21.0 g were weighed out and mixed in a plastic bag. The powder mixture was introduced into the powder supply feeder of a double screw wet granulator. The powder mixture was fed at a rate of 20 kg/hour from the powder supply feeder into the chamber, and as 8.5 wt % polyvinyl alcohol aqueous solution was fed therein at a rate of 80 g/min by a peristaltic pump, granulation was continuously carried out for 1.5 minutes at a screw speed of 700 rpm using the screw structure shown in Table 13. The granulated powder was dried in a fluid bed dryer. 455 g of the dried powder was sized at 1200 rpm using a sizer (brand name: Quadro Comil 197S, by Powrex Corporation), with a grater-type screen (mesh size 1.06 mm) and a compression-type blade. To 396 g of the resulting sized powder, magnesium stearate 4.0 g was added and mixed. In the post-tableting process, FC tablets were obtained in the same manner as in Example 4.

Example 17: Obeticholic Acid 10 mg FC Tablets (Double Screw Wet Granulation Method)

Obeticholic acid 50.0 g, lactose hydrate 468.0 g, partly pre-gelatinized starch (Starch 1500: by Colorcon) 140.0 g, and crospovidone 21.0 g were weighed out and mixed in a plastic bag. The powder mixture was introduced into the powder supply feeder of a double screw wet granulator. The powder mixture was fed at a rate of 20 kg/hour from the powder supply feeder into the chamber, and as 13.8 wt % polyvinyl alcohol aqueous solution was fed therein at a rate of 50 g/min by a peristaltic pump, granulation was continuously carried out for 1.5 minutes at a screw speed of 700 rpm using the screw structure shown in Table 13. The granulated powder was dried in a fluid bed dryer. 489 g of the dried powder was sized at 1200 rpm using a sizer (brand name: Quadro Comil 197S, by Powrex Corporation), with a grater-type screen (mesh size 1.06 mm) and a compression-type blade. To 396 g of the resulting sized powder, magnesium stearate 4.0 g was added and mixed. In the post-tableting process. FC tablets were obtained in the same manner as in Example 4.

Table 14 shows the formulations of the obeticholic acid FC tablets obtained in Examples 15-17.

TABLE 14

Formulation of obeticholic acid FC tablets (mg)

| Component | Example 15 | Example 16 | Example 17 |
|---|---|---|---|
| Obeticholic acid | 20.0 | 10.0 | 10.0 |
| Lactose | 94.8 | 104.8 | 93.6 |
| Partly pre-gelatinized starch | — | — | 28.0 |
| Low-substituted hydroxypropyl cellulose | 16.8 | 16.8 | — |
| Crospovidone | 4.2 | 4.2 | 4.2 |
| Polyvinyl alcohol (partially saponified product) | 2.8 | 2.8 | 2.8 |
| Magnesium stearate (plant-derived) | 1.4 | 1.4 | 1.4 |
| Hydroxypropylmethyl cellulose | 3.00 | 3.00 | 3.00 |
| Talc | 0.61 | 0.61 | — |
| Titanium oxide | 0.24 | 0.24 | 0.85 |
| Triethyl citrate | 0.15 | 0.15 | 0.15 |
| Carnauba wax | trace amount | trace amount | trace amount |
| Total | 144.0 | 144.0 | 144.0 |

Table 15 shows the results of dissolution tests carried out in accordance with Test Example 1 on the obeticholic acid FC tablets of Examples 15-17. Table 15 shows that the dissolution of the obeticholic acid-containing tablets was extremely fast and that exceptional quick-release tablets were obtained even with the double screw wet granulation method.

TABLE 15

Dissolution tests of obeticholic acid FC tablets (dissolution rate: %)

| | 0 | 10 | 15 | 30 | 60 | 120 |
|---|---|---|---|---|---|---|
| Example 15 | 0.0 | 51.8 | 58.9 | 74.6 | 86.0 | 92.8 |
| Example 16 | 0.0 | 74.4 | 83.7 | 92.7 | 96.1 | 97.3 |
| Example 17 | 0.0 | 53.1 | 70.5 | 86.3 | 94.8 | 97.5 |

(Batch-Type Granulation Method: Elution Stability of Preparation Obtained with Fluid Bed Granulation Method)

The post-storage elution of the obeticholic acid FC tablets of Examples 4 and 14 (obtained using a fluid bed granulator) was assessed. Tables 16 and 17 as well as FIGS. 4 and 5 show the results of the assessment of elution in accordance with Test Example 1 after each type of tablet had been placed in brown vials and stored open for 1 and 3 months at 40° C. and 75% RH. The results revealed that there were no delays in elution, even under harsh humidity conditions, indicating that exceptional quick-release tablets were obtained.

TABLE 16

Dissolution tests of obeticholic acid FC tablets after open storage at 40° C. and 75% RH (dissolution rate: %)

| | Storage period | 0 | 10 | 15 | 30 | 60 | 120 |
|---|---|---|---|---|---|---|---|
| Example 4 | Initial | 0.0 | 53.7 | 63.6 | 78.4 | 89.2 | 94.9 |
| Example 4 | 1 M | 0.0 | 51.1 | 60.4 | 75.0 | 87.1 | 93.0 |
| Example 4 | 3 M | 0.0 | 52.3 | 61.9 | 76.7 | 88.8 | 93.0 |

TABLE 17

Dissolution tests of obeticholic acid FC tablets after open storage at 40° C. and 75% RH (dissolution rate: %)

| | Storage period | 0 | 10 | 15 | 30 | 60 | 120 |
|---|---|---|---|---|---|---|---|
| Example 14 | Initial | 0.0 | 51.5 | 59.1 | 74.7 | 87.8 | 95.3 |
| Example 14 | 1 M | 0.0 | 54.6 | 64.5 | 80.3 | 90.9 | 95.6 |
| Example 14 | 3 M | 0.0 | 56.0 | 65.1 | 81.0 | 91.4 | 97.2 |

(Continuous Granulation Method: Elution Stability of Preparation Obtained with Double Screw Wet Granulation Method)

The post-storage elution of the obeticholic acid FC tablets of Examples 16 and 17 (obtained using a double screw wet granulator) was assessed. Tables 18 and 19 as well as FIGS. 6 and 7 show the results of the assessment of elution in accordance with Test Example 1 after each type of tablet had been placed in brown vials and stored open for 1 and 3 months at 40° C. and 75% RH. The results revealed that there were no substantial delays in elution, even under harsh humidity conditions, indicating that exceptional quick-release tablets were obtained. Even better elution stability was shown in Example 17, in which partly pre-gelatinized starch was used as the disintegrating agent.

TABLE 18

Dissolution tests of obeticholic acid FC tablets after open storage at 40° C. and 75% RH (dissolution rate: %)

| | Storage period | 0 | 10 | 15 | 30 | 60 | 120 |
|---|---|---|---|---|---|---|---|
| Example 16 | Initial | 0.0 | 74.4 | 83.7 | 92.7 | 96.1 | 97.3 |
| Example 16 | 1 M | 0.0 | 56.9 | 67.1 | 80.3 | 90.2 | 94.5 |
| Example 16 | 3 M | 0.0 | 52.3 | 65.3 | 78.8 | 89.7 | 95.7 |

TABLE 19

Dissolution tests of obeticholic acid FC tablets after open storage at 40° C. and 75% RH (dissolution rate: %)

| | Storage period | 0 | 10 | 15 | 30 | 60 | 120 |
|---|---|---|---|---|---|---|---|
| Example 17 | Initial | 0.0 | 53.1 | 70.5 | 86.3 | 94.8 | 97.5 |
| Example 17 | 1 M | 0.0 | 49.7 | 67.8 | 80.4 | 91.8 | 96.1 |
| Example 17 | 3 M | 0.0 | 45.0 | 65.4 | 78.1 | 91.1 | 96.2 |

(Assessment of Stability of Amorphous Form)

Example 18 below was assessed to see whether there are any changes in stability (whether crystallization occurs) when the amorphous form of obeticholic acid is used, that is, stability being understood as the retention of the amorphous form even after wet granulation and long-term storage in tablet form.

Example 18

X-ray powder diffraction was carried out to see whether, in cases where the amorphous form of obeticholic acid was used, the amorphous form was retained even after wet granulation. The assessments were carried out using the initially prepared (initial) product of the obeticholic acid FC tablet preparation in Example 4, two stored products of the preparation in Example 4 (6 months of closed storage at 40° C. and 75% RH, and 3 months of open storage at 40l and 75% RH), and placebo film-coated (FC) tablets. The placebo FC tablets were prepared in the same manner as in Example 4, except that the obeticholic acid content per tablet in Example 4 was changed to 0 mg, and lactose was used to adjust for the reduced content.

The samples were then analyzed by non-destructive X-ray powder diffraction, with the tablet dosage form left intact. Measurements were carried out at SPring-8, a large-scale synchrotron radiation (X-ray) facility in Harima Science Garden City, Hyogo Prefecture. FIG. 8 shows the various peak shapes on XRPD (shown in descending order: placebo FC tablets, the initial product of Example 4, the products stored closed for 6 months at 40° C. and 75% RH, and the products stored open for 3 months at 40° C. and 75% RH). In FIG. 9, the peak shapes of FIG. 8 are superimposed over each other.

In a comparative test using these XRPD results, the sharp peaks confirmed as belonging to the placebo FC tablet were attributed to crystals of inactive ingredients that were not obeticholic acid. The peak attributable to the amorphous form of obeticholic acid comprised an extremely broad peak with only a broadly humped baseline (commonly referred to as a halo pattern). In this test, baseline in the XRPD peak shapes of the three samples other than the placebo FC tablets was higher than baseline of the placebo FC tablets, the three shapes were consistent with each other, and there were no new sharp peaks of obeticholic crystals attributable to the transformation of obeticholic acid into crystals (that is, there were no sharp peaks other than the peaks attributable to the placebo FC tablets), thus confirming that the amorphous form had been retained in the three samples.

The results in FIGS. 8 and 9 show that the obeticholic acid FC tablets of the present invention, not only the initial product but also the two stored products, had no sharp peaks other than the peaks attributable to the placebo FC tablets, and had a consistent halo pattern shape, thus confirming that the amorphous form of obeticholic acid had been retained, even after wet granulation and long-term tablet storage under humid conditions.

(Assessment of Chemical Stability)

The following assessments were carried out to see whether, in cases where the amorphous form of obeticholic acid was used, there were any changes in chemical stability even after wet granulation. Specifically, measurements were taken of the amounts in which obeticholic acid dimers were produced (referred to in Patent Document 2 as "Impurity 6," "3α (3α, 7α-dihydroxy-6α-ethyl-5β-cholan-24-oyloxy)-7α-hydroxy-6α-ethyl-5β-cholan-24-oic acid," and "6ECDCA dimer"), which were confirmed to have a high propensity to increase in the preparation process and stability tests among known related substances of obeticholic acid disclosed in Patent Document 2, for example.

Example 19: Stability of Obeticholic Acid (Active Pharmaceutical Ingredient)

5 mg of obeticholic acid (active pharmaceutical ingredient, amorphous) was weighed out into a test tube.

<Storage>

Test tubes containing the obeticholic acid prepared in Example 19 and the obeticholic acid 20 mg FC tablets of Example 4 were stored under the following conditions. The amounts in which obeticholic acid dimer was produced before (initial) and after storage were measured in accordance with Test Example 3.

4 weeks at 50° C. and 85% RH (open)
4 weeks at 60° C. (closed)

Test Example 3

<Preparation of Sample Solution>

Samples of Active Pharmaceutical Ingredient of Example 19:

Acetonitrile/water (9/1) was added in an amount of exactly 10 mL to test tubes that had been retrieved from storage, and the contents were ultrasonically treated to extract the obeticholic acid. Following centrifugation (10 min at 3000 rpm), the supernatant was made into samples for HPLC assay (500 μg/mL obeticholic acid).

Samples of FC Tablets of Example 4:

One tablet containing 20 mg obeticholic acid (per tablet) that had been retrieved from storage was introduced into a 40 mL graduated measuring flask. Acetonitrile/water (9/1) was added to the graduated measuring flask, the contents were ultrasonically treated (10 min), and it was confirmed that the tablet had disintegrated. The contents were thoroughly shaken (60 min at 300 rpm) using a shaker, and were again ultrasonically treated to extract the obeticholic acid. Acetonitrile/water (9/1) were added to a constant volume, followed by centrifugation (10 min at 3000 rpm), and the supernatant was made into samples for HPLC assay (500 µg/mL).

<Preparation of Standard Solution>

50 mg of obeticholic acid was weighed out into a 100 mL graduated measuring flask and dissolved using acetonitrile/water (9/1) (500 µg/mL). The resulting solution was diluted with acetonitrile/water (9/1) to prepare 15.0 µg/mL (3.0%), 5.0 µg/mL (1.0%), and 0.25 µg/mL (0.05%) standard solutions.

<Quantification>

The above three standard solutions were used to produce a calibration curve, and the obeticholic acid dimer contained in the sample solutions was quantified. The conditions of analysis are shown below.

<Conditions of Analysis>

Detector: Charged particle detector
Column: by Sigma-Aldrich, SUPELCO Discovery C8 (particle size: 5 µm; internal
diameter: 4.6 mm; length: 15 cm)
Mobile phase: Acetonitrile/methanol/acetic acid aqueous solution (pH 3.0) mixture (8/1/1)
Analysis time: 15 min
Flow rate: 1.0 mL/min.
Column temperature: 30° C.
Injection volume: 100 µL
Sample cooler temperature: 10° C.
Syringe cleaning solution: Acetonitrile/methanol/acetic acid aqueous solution (pH 3.0) mixture (8/1/1)
Sample-dissolving solvent: Acetonitrile water (9/1)
Charged particle detector parameters
Gas: Nitrogen
Gas pressure: 35 psi
Range: 100 pA
Filter: High <Results>

The results of the assessments of the samples in Examples 4 and 19 are shown in Tables 20 and 21. The increase in obeticholic acid dimer before and after wet granulation, as assessed by comparing the pre-wet granulation obeticholic acid active pharmaceutical ingredient alone (Example 19) and the wet granulated obeticholic acid 20 mg FC tablets (Example 14), was virtually the same, less than 0.1% in both samples, which were acceptable levels for practical purposes in the preparation. Of further interest was the fact that the rate of increase in obeticholic acid dimer after storage under the two sets of stringent conditions was virtually the same in the pre-wet granulation obeticholic acid active pharmaceutical ingredient (Example 19) and the wet granulated obeticholic acid 20 mg FC tablets (Example 4). Specifically, it was confirmed that the chemical stability of the obeticholic acid FC tablets of the present invention was the same after wet granulation as before wet granulation. Compounds in contact with other blended components in preparations usually tend to be less stable than the pharmaceutically active ingredient alone, and this is an unexpected effect, given that the present compound is amorphous and is wet granulated.

The manufacture of the preparation of the present application, which is obtained using a wet granulation method for amorphous obeticholic acid, surprisingly allowed a preparation having exceptional elutability, for example, as noted above, to be provided without compromising the stability in the two senses noted above (compound decomposition and change to crystal form).

TABLE 20

Amount of obeticholic acid dimer production (%)

| | | Initial | 50° C., 85% RH open 4 W | 60° C. closed 4 W |
|---|---|---|---|---|
| Example 19 | Obeticholic acid active pharmaceutical ingredient | 0.04 | 0.83 | 0.81 |
| Example 4 | Obeticholic acid 20 mg FC tablets | 0.08 | 0.71 | 0.78 |

TABLE 21

Increase (%) in obeticholic acid dimer from initial product

| | | 50° C., 85% RH open 4 W | 60° C. closed 4 W |
|---|---|---|---|
| Example 19 | Obeticholic acid active pharmaceutical ingredient | 0.79 | 0.77 |
| Example 4 | Obeticholic acid 20 mg FC tablets | 0.63 | 0.70 |

Example 20: Obeticholic Acid 10 mg FC Tablets (Double Screw Wet Granulation Method)

(1) Granulation-Mixing

Obeticholic acid 62.22 g (corrected for potency), lactose 569.74 g (lactose used to adjust for corrected portion) 80 g, partially pre-gelatinized starch 170.80 g, crospovidone 25.62 g, and polyvinyl alcohol (partially saponified product) 8.54 g were weighed out, and were mixed for 15 min in a small V mixer. The powder mixture was pulverized at 2400 rpm in a pulverizing mill (brand name: Quadro Comil 197S, by Powrex Corporation), using a round screen (mesh size 0.99 mm) and a shearing-type blade, and was further mixed for 15 min in a small V mixer. The powder mixture was introduced into the powder supply feeder of a double screw wet granulator. The powder mixture was fed at a rate of 20 kg/hour from the powder supply feeder into the chamber, and as 6.7 wt % polyvinyl alcohol aqueous solution was fed therein at a rate of 50 g/min by a peristaltic pump, granulation was continuously carried out for 1.5 minutes at a screw speed of 700 rpm using the screw structure shown in Table 13. The granulated powder was dried in a fluid bed dryer. 441.73 g of the dried powder was sized at 2400 rpm using a sizer (brand name: Quadro Comil 197S, by Powrex Corporation), with a grater-type screen (mesh size 1.016 mm) and a shearing-type blade. To 400 g of the resulting sized powder, magnesium stearate 4.04 g was added and mixed to prepare granules for tableting.

(2) Tableting:

The tableting granules prepared in (1) above were tableted under the following conditions using a rotary tablet press (VEL2, by Kikusui Seisakusho Ltd.) to obtain approximately 140 mg uncoated tablets (per tablet).
Punch: Round-faced (R) tablet
Punch size: φ7 mm, 10 R
Disk revolutions: 30 rpm
Tableter compression pressure: Tablets were prepared to a tablet hardness of 60 to 120 N.
(3) Coating:

A coating solution was prepared in the same manner as in Example 4. The uncoated tablets prepared in (2) above were coated under the following conditions to a coating agent film quantity of approximately 4 mg using a Hi-Coater LABO (by Freund Corporation), giving FC tablets. Carnauba wax was added after the drying step in the film coating process.
<FC Conditions>
Charge air temperature: 70° C.
Air flow: 0.5 m³/min
Pan revolutions: 21 rpm
Spray pressure: 0.12 MPa
Solution rate: 3-5 g/min

Example 21: Obeticholic Acid 25 mg FC Tablets (Double Screw Wet Granulation Method)

Obeticholic acid 250 g, lactose 786 g, partly pre-gelatinized starch 280 g, crospovidone 42 g, and polyvinyl alcohol (partially saponified product) 14 g were weighed out to obtain FC tablets in the same manner as in Example 20.

Example 22: Obeticholic Acid 25 mg FC Tablets (Double Screw Wet Granulation Method)

Obeticholic acid 200 g, lactose 836 g, partly pre-gelatinized starch 280 g, crospovidone 42 g. and polyvinyl alcohol (partially saponified product) 14 g were weighed out to obtain granules for tableting in the same manner as in Example 20. The granules for tableting were used to prepare approximately 175 mg uncoated tablets (per tablet) using a rotary tablet press (VEL2, by Kikusui Seisakusho), with an 48.0 mm round 12.0 R punch and disk revolutions 30 rpm. In the FC process, the tablets were coated to a film quantity of approximately 5 mg in the same manner as in Example 20, giving FC tablets.

Example 23: Obeticholic Acid 25 mg FC Tablets (Double Screw Wet Granulation Method)

Obeticholic acid 250 mg, lactose 898 g, low-substituted hydroxypropyl cellulose 168 g, and crospovidone 42 g were weighed out, and 8.5 wt % polyvinyl alcohol aqueous solution was fed at a rate of 80 g/min by a peristaltic pump, but FC tablets were otherwise obtained in the same manner as in Example 20.

Example 24: Obeticholic Acid 25 mg FC Tablets (Double Screw Wet Granulation Method)

Obeticholic acid 200 mg, lactose 948 g, low-substituted hydroxypropyl cellulose 168 g, and crospovidone 42 g were weighed out, and 8.5 wt % polyvinyl alcohol aqueous solution was fed at a rate of 80 g/min by a peristaltic pump, but granules for tableting were otherwise prepared in the same manner as in Example 20. The granules for tableting were used to prepare approximately 175 mg uncoated tablets (per tablet) using a rotary tablet press (VEL2, by Kikusui Seisakusho), with an 08.0 mm round 12.0 R punch and disk revolutions 30 rpm. In the FC process, the tablets were coated to a film quantity of approximately 5 mg in the same manner as in Example 20, giving FC tablets.

Table 22 shows the formulations of the obeticholic acid FC tablets obtained in Examples 20-24.

TABLE 22

Obeticholic acid FC tablet formulation (mg)

| Ingredients | Ex. 20 | Ex. 21 | Ex. 22 | Ex. 23 | Ex. 24 |
| --- | --- | --- | --- | --- | --- |
| Obeticholic acid | 10.0 | 25.0 | 25.0 | 25.0 | 25.0 |
| Lactose | 93.6 | 78.6 | 104 | 89.8 | 118.5 |
| Partly pre-gelatnized starch | 28.0 | 28.0 | 35.0 | — | — |
| Low-substituted hydroxypropyl cellulose | — | — | — | 16.8 | 21.0 |
| Crospovidone | 4.2 | 4.2 | 5.25 | 4.2 | 5.25 |
| Polyvinyl alcohol (partially saponified) | 2.8 | 2.8 | 3.5 | 2.8 | 3.5 |
| Magnesium stearate (plant-derived) | 1.4 | 1.4 | 1.75 | 1.4 | 1.75 |
| Hydroxypropyl-methyl cellulose | 3.00 | 3.00 | 3.75 | 3.00 | 3.75 |
| Talc | 0.61 | 0.61 | 0.7625 | 0.61 | 0.7625 |
| Titanium oxide | 0.24 | 0.24 | 0.30 | 0.24 | 0.30 |
| Triethyl citrate | 0.15 | 0.15 | 0.1875 | 0.15 | 0.1875 |
| Carnauba wax | Low amount | Low amount | Low amount | Low amount | Low amount |
| Total | 144.0 | 144.0 | 180.0 | 144.0 | 180.0 |

Table 23 shows the results of dissolution tests carried out in accordance with Test Example 1 on the obeticholic acid FC tablets of Example 20. Table 23 shows that the dissolution of the obeticholic acid-containing tablets was extremely fast and that exceptional quick-release tablets were obtained. Dissolution tests performed in accordance with Test Example 1 on the obeticholic acid FC tables of Examples 21-24 confirmed the same results.

TABLE 23

Obeticholic acid FC tablet dissolution test (dissolution rate: %)

| | 0 | 10 | 15 | 30 | 60 | 120 |
| --- | --- | --- | --- | --- | --- | --- |
| Example 21 | 0.0 | 69.4 | 80.5 | 91.9 | 96.4 | 97.5 |

Analysis of the concentration of obeticholic acid in blood samples in a pharmacokinetics study of oral administration of the preparation of the present invention in humans showed that the preparation of the present invention was associated with favorable pharmacokinetics and far better bioavailability than conventional preparations.

The invention claimed is:
1. An oral preparation, comprising obeticholic acid or a pharmacologically acceptable salt thereof, (i) a water-soluble excipient, wherein the water-soluble excipient is a sugar or a sugar alcohol; (ii) a disintegrating agent, wherein the disintegrating agent is selected from any one or more of a starch, sodium croscarmellose, carmellose, low-substituted hydroxypropyl cellulose, and crospovidone; and (iii) a water-soluble polymer binder, wherein the water-soluble polymer binder is a polyvinyl alcohol-based resin, wherein the preparation is a quick-release tablet.

2. The oral preparation of claim 1, wherein the sugar or sugar alcohol is mannitol or lactose.

3. The oral preparation of claim 1, wherein the starch is a pre-gelatinized starch.

4. The oral preparation of claim 3, wherein the pre-gelatinized starch is a partly pre-gelatinized starch.

5. The oral preparation of claim 1, wherein the disintegrating agent comprises two different types, (iia) a disintegrating agent A and (iib) a disintegrating agent B.

6. The oral preparation of claim 5, wherein the disintegrating agent A is selected from a starch, sodium croscarmellose, carmellose, calcium carmellose, sodium carmellose, crospovidone, low-substituted hydroxypropyl cellulose, and sodium carboxymethyl starch, and the disintegrating agent B is any disintegrating agent other than the disintegrating agent A, selected from a starch, sodium croscarmellose, carmellose, calcium carmellose, sodium carmellose, crospovidone, low-substituted hydroxypropyl cellulose, and sodium carboxymethyl starch.

7. The oral preparation of claim 6, wherein the disintegrating agent A is a starch.

8. The oral preparation of claim 7, wherein the starch is a pre-gelatinized starch or partly pre-gelatinized starch.

9. The oral preparation of claim 6, wherein the disintegrating agent A is low-substituted hydroxypropyl cellulose.

10. The oral preparation of claim 6, wherein the disintegrating agent B is any of crospovidone, sodium croscarmellose, or sodium carboxymethyl starch.

11. The oral preparation of claim 10, wherein the disintegrating agent B is crospovidone.

12. The oral preparation of claim 1, wherein the polyvinyl alcohol-based resin is a polyvinyl alcohol, polyvinyl alcohol derivative, or polyvinyl alcohol copolymer.

13. The oral preparation of claim 1, wherein the obeticholic acid or pharmacologically acceptable salt thereof is an amorphous form.

14. The oral preparation of claim 1, wherein the obeticholic acid or pharmacologically acceptable salt thereof is obeticholic acid.

* * * * *